(12) United States Patent
Weisman et al.

(10) Patent No.: US 11,433,158 B2
(45) Date of Patent: Sep. 6, 2022

(54) RECYCLE FRIENDLY AND SUSTAINABLE ABSORBENT ARTICLES

(71) Applicant: The Procter & Gamble Company, Cincinnati, OH (US)

(72) Inventors: Paul Thomas Weisman, Cincinnati, OH (US); Eric Patton Weinberger, Fairfield, OH (US)

(73) Assignee: The Procter & Gamble Company, Cincinnati, OH (US)

(*) Notice: Subject to any disclaimer, the term of this patent is extended or adjusted under 35 U.S.C. 154(b) by 733 days.

(21) Appl. No.: 16/207,327

(22) Filed: Dec. 3, 2018

(65) Prior Publication Data

US 2019/0192723 A1  Jun. 27, 2019

Related U.S. Application Data

(60) Provisional application No. 62/597,539, filed on Dec. 12, 2017.

(51) Int. Cl.
| | | |
|---|---|---|
| *A61F 13/15* | (2006.01) | |
| *A61L 15/24* | (2006.01) | |
| *A61L 15/60* | (2006.01) | |
| *A61L 15/62* | (2006.01) | |
| *A61F 13/53* | (2006.01) | |

(52) U.S. Cl.
CPC ............. *A61L 15/24* (2013.01); *A61F 13/53* (2013.01); *A61L 15/60* (2013.01); *A61L 15/62* (2013.01); *A61F 2013/530481* (2013.01)

(58) Field of Classification Search
CPC ........ A61F 13/15252; A61F 2013/1526; A61F 2013/51433; A61F 2013/530313; A61F 2013/530321
See application file for complete search history.

(56) References Cited

U.S. PATENT DOCUMENTS

| | | | |
|---|---|---|---|
| 4,519,798 A | 5/1985 | Dinius | |
| 4,937,299 A | 6/1990 | Ewen et al. | |
| 5,218,071 A | 6/1993 | Tsutsui et al. | |
| 5,272,236 A | 12/1993 | Lai et al. | |

(Continued)

FOREIGN PATENT DOCUMENTS

| | | |
|---|---|---|
| WO | 9606587 A1 | 3/1996 |
| WO | 2007109128 A2 | 9/2007 |

(Continued)

OTHER PUBLICATIONS

Extended European Search Report and Search Opinion; Application No. 18212088.1 dated May 8, 2019; 9 pages.

*Primary Examiner* — Catharine L Anderson
(74) *Attorney, Agent, or Firm* — Amanda Herman Berghauer; Brian M. Bolam

(57) ABSTRACT

An absorbent article comprising a topsheet, a backsheet joined to the topsheet, and an absorbent core positioned intermediate the topsheet and the backsheet and comprising a core absorbent material, in which the core absorbent material comprises superabsorbent polymers with a bio-based content from about 5% to about 100% using ASTM D6866-10, method B and the absorbent article comprises a polyolefin content of at least about 90% by weight, based on a total weight of the absorbent article excluding the core absorbent material.

19 Claims, 15 Drawing Sheets

(56) References Cited

U.S. PATENT DOCUMENTS

| | | |
|---|---|---|
| 5,278,272 A | 1/1994 | Lai et al. |
| 5,304,161 A | 4/1994 | Noel et al. |
| 5,322,728 A | 6/1994 | Davey et al. |
| 5,439,458 A | 8/1995 | Noel et al. |
| 5,472,775 A | 12/1995 | Obijeski et al. |
| 5,539,056 A | 7/1996 | Yang et al. |
| 5,571,619 A | 11/1996 | McAlpin et al. |
| 5,596,052 A | 1/1997 | Resconi et al. |
| 5,628,097 A | 5/1997 | Benson et al. |
| 6,090,325 A | 7/2000 | Wheat et al. |
| 6,198,018 B1 | 3/2001 | Curro |
| 6,500,563 B1 | 12/2002 | Datta et al. |
| 6,645,190 B1 | 11/2003 | Olson et al. |
| 6,677,258 B2 | 1/2004 | Carroll et al. |
| 6,761,711 B1 | 7/2004 | Fletcher et al. |
| 6,817,994 B2 | 11/2004 | Popp et al. |
| 6,840,928 B2 | 1/2005 | Datta et al. |
| 6,849,067 B2 | 2/2005 | Fletcher et al. |
| 6,893,426 B1 | 5/2005 | Popp et al. |
| 6,953,452 B2 | 10/2005 | Popp et al. |
| 6,969,377 B2 | 11/2005 | Koele et al. |
| 7,156,833 B2 | 1/2007 | Couture-Dorschner et al. |
| 7,201,744 B2 | 4/2007 | Van Gompel et al. |
| 7,497,851 B2 | 3/2009 | Koele et al. |
| 7,682,349 B2 | 3/2010 | Popp et al. |
| 7,862,550 B2 | 1/2011 | Koele et al. |
| 7,901,393 B2 | 3/2011 | Matsuda et al. |
| 8,007,485 B2 | 8/2011 | Popp et al. |
| 8,361,048 B2 | 1/2013 | Kuen et al. |
| 8,372,052 B2 | 2/2013 | Popp et al. |
| 8,461,129 B2 * | 6/2013 | Bolduc ................ A61L 15/28 514/54 |
| 8,579,876 B2 | 11/2013 | Popp et al. |
| 8,676,549 B2 * | 3/2014 | Weisman .......... A61F 13/55115 703/2 |
| 8,703,450 B2 | 4/2014 | Bub et al. |
| 8,747,379 B2 | 6/2014 | Fletcher et al. |
| 8,785,716 B2 | 7/2014 | Schäfer et al. |
| 8,883,076 B2 | 11/2014 | Somma et al. |
| 8,940,205 B2 * | 1/2015 | Keller ................ B29B 17/0036 264/140 |
| 8,979,005 B2 | 3/2015 | Somma et al. |
| 9,045,577 B2 * | 6/2015 | Devisme ............... C08F 210/16 |
| 9,095,853 B2 | 8/2015 | Somma et al. |
| 9,156,034 B2 | 10/2015 | Somma et al. |
| 9,169,366 B2 | 10/2015 | Weisman et al. |
| 9,241,843 B2 | 1/2016 | Bunnelle et al. |
| 9,511,168 B2 * | 12/2016 | Zhang .................... A61L 15/60 |
| 9,630,901 B2 | 4/2017 | Godlewski et al. |
| 9,822,197 B2 | 11/2017 | Horner et al. |
| 9,850,192 B2 * | 12/2017 | Harris ...................... C12P 7/42 |
| 10,493,661 B2 * | 12/2019 | Lee ......................... B29B 17/02 |
| 10,500,104 B2 * | 12/2019 | Sookraj ............. A61F 13/15252 |
| 2007/0219521 A1 | 9/2007 | Hird et al. |
| 2011/0139657 A1 | 6/2011 | Hird et al. |
| 2011/0139658 A1 | 6/2011 | Hird et al. |
| 2011/0139659 A1 | 6/2011 | Hird et al. |
| 2011/0139662 A1 | 6/2011 | Hird et al. |
| 2011/0152812 A1 | 6/2011 | Hird et al. |
| 2011/0319849 A1 * | 12/2011 | Collias ................... A61L 15/60 604/372 |
| 2013/0144239 A1 | 6/2013 | Warren et al. |
| 2013/0211363 A1 | 8/2013 | LaVon et al. |
| 2013/0273384 A1 * | 10/2013 | Godlewski .............. C08F 20/06 522/182 |
| 2014/0378924 A1 | 12/2014 | Turner et al. |
| 2015/0173958 A1 | 6/2015 | Bunnelle et al. |
| 2015/0374876 A1 * | 12/2015 | Hubbard, Jr. ...... B01J 20/28054 502/402 |
| 2016/0101208 A1 | 4/2016 | Topolkaraev et al. |
| 2016/0114071 A1 | 4/2016 | Topolkaraev et al. |
| 2016/0115291 A1 | 4/2016 | Topolkaraev et al. |
| 2016/0122484 A1 | 5/2016 | Topolkaraev et al. |
| 2016/0130731 A1 | 5/2016 | Topolkaraev et al. |
| 2016/0136014 A1 | 5/2016 | Arora et al. |
| 2016/0206774 A1 | 7/2016 | Hird |
| 2017/0056253 A1 * | 3/2017 | Chester ................ A61F 13/511 |
| 2017/0203542 A1 | 7/2017 | Ramaratnam et al. |
| 2018/0051404 A1 * | 2/2018 | Novarino ................ D01D 5/38 |
| 2020/0001506 A1 * | 1/2020 | Konishi ................ B29C 48/277 |

FOREIGN PATENT DOCUMENTS

| | | |
|---|---|---|
| WO | 2016023016 A1 | 2/2016 |
| WO | WO2016085709 A1 | 6/2016 |
| WO | WO2016085711 A1 | 6/2016 |

* cited by examiner

RECYCLE FRIENDLY AND SUSTAINABLE ABSORBENT ARTICLES

FIELD

The present disclosure is directed to absorbent articles, and more particularly to absorbent articles comprising one or more components that are recycle friendly and comprise bio-based, sustainable materials.

BACKGROUND

Absorbent articles typically comprise a topsheet, a backsheet, and an absorbent core disposed between the topsheet and the backsheet. The absorbent article may also comprise an acquisition layer that temporarily stores liquid bodily exudates received from the topsheet before being received by the absorbent core. The absorbent core typically comprises superabsorbent polymer particles that absorb and store the liquid bodily exudates.

Absorbent articles typically comprise a wide variety of different materials, including plastic films, foam, superabsorbent polymer particles, natural materials such as cellulose fiber, etc., many of which may be bonded or joined together. Due to the presence of bodily exudates and the cost and difficulty associated with separating the component materials and rendering them suitable for reuse, used absorbent articles have typically been excluded from the stream of waste products for differential collection and recycling. As a result, most used absorbent articles are currently disposed of as regular, undifferentiated waste. The proliferation of regulations limiting landfill waste, along with rising costs, have made traditional disposal of waste in landfills less desirable. In addition, global demand for absorbent articles is expected to rise due to increasing birth rates in developing countries, rising household incomes, and a growing aging population. The growing demand for absorbent articles will further exacerbate the amount of absorbent articles going to landfill. Communities around the globe are seeking solutions to the growing waste stream of used absorbent articles. Furthermore, there is global interest in creating a circular economy in various parts of the world by instituting materials recycling programs for metals, plastics, packaging materials, and other materials and/or products, including absorbent articles. However, many obstacles remain to achieving meaningful levels of recycling for used absorbent articles. For example, in order for recycling to be technologically and economically feasible, each different material of the absorbent article requires a suitable recycling process or material-specific separation means within the overall recycling process and an appropriate end use and/or market for the separated recycled material. The more materials to be separated in the absorbent article recycling operation, the more complex and expensive the recycling operation becomes. In addition, conventional, non-recyclable materials that are currently used in the manufacture of absorbent articles possess certain desired characteristics (e.g., softness, breathability, processability, etc.), and recyclable materials must provide these same characteristics as well to be acceptable substitutes.

In addition, the vast majority of commercially available absorbent articles, such as diapers, contain a significant amount of petrochemicals or polymers or other materials derived from petrochemicals. For example, most mass-produced diapers include fibrous outer layers, topsheet components, core wrap components, cuffs, and other fibrous layers or components that generally contain petroleum-based fibers and a liquid barrier layer or other film components made from a petroleum-based polymers or materials. Additionally, most mass-produced absorbent articles, such as diapers comprise include superabsorbent polymers derived from petroleum-based polymers or materials. However, fossil fuels are a finite resource and global demand for petroleum continues to increase due to growing populations and increasing standards of living worldwide.

Given there may be a limited amount of petroleum in the world, it is prudent to create absorbent articles which are more readily recycled, are designed for simple recycling, or designed to be friendly in a recycling operation. Additionally, the absorbent article design should be from materials derived from bio-based means or means which are not dependent upon materials for chemicals derived from petroleum sources. Furthermore, consumers are interested in purchasing absorbent articles, such as diapers, which are environmentally friendly, green, or made from sustainable sources and are also designed to be recycle friendly. Net, there is a need for absorbent articles with improved recyclability and sustainability.

SUMMARY

The present disclosure provides absorbent articles comprising a high content of a recyclable material, such as one or more polyolefins, and one or more components comprising bio-based materials. Some current absorbent articles contain one or more components comprising a polyolefin. However, these absorbent articles typically also contain multiple other types of recyclable and non-recyclable plastics and other materials. Each of these different materials must be separated, and a suitable recycling stream must be found for each material. Reducing the number of different materials contained in the absorbent article enhances recyclability by simplifying the separation process and decreasing the number of recycling streams, while yielding high purity recycled components. In addition, increasing the amount of content derived from sustainable, bio-based sources helps to alleviate demand for non-renewable resources and meets the growing consumer demand for absorbent articles, such as diapers, which are made with sustainable materials.

In accordance with an aspect of the present disclosure, an absorbent article is provided comprising: a topsheet; a backsheet joined to the topsheet; and an absorbent core positioned intermediate the topsheet and the backsheet and comprising a core absorbent material. The core absorbent material may comprise superabsorbent polymers with a bio-based content from about 5% to about 100% using ASTM D6866-10, method B. The absorbent article may comprise a polyolefin content of at least about 90% by weight, based on a total weight of the absorbent article excluding the core absorbent material.

The polyolefin content may comprise at least about 95% by weight or at least about 97% by weight or at least about 99% by weight, based on the total weight of the absorbent article excluding the core absorbent material.

The bio-based content of the superabsorbent polymers may comprise from about 10% to about 100% or from about 25% to about 100% or from about 40% to about 100% or from about 50% to about 100% or from about 75% to about 100% or from about 90% to about 100%, using ASTM D6866-10, method B.

The core absorbent material may comprise at least about 60% by weight or at least about 70% by weight or at least about 90% by weight of the superabsorbent polymers.

In some example, the core absorbent material may be substantially free of absorbent pulp. In other examples, the core absorbent material may further comprise an absorbent pulp.

The topsheet may comprise a bio-based polyolefin with a bio-based content from about 5% to about 100% or from about 10% to about 100% or from about 25% to about 100% or from about 40% to about 100% or from about 50% to about 100% or from about 75% to about 100% or from about 90% to about 100%, using ASTM D6866-10, method B.

The backsheet may comprise a bio-based polyolefin with a bio-based content from about 5% to about 100% or from about 10% to about 100% or from about 25% to about 100% or from about 40% to about 100% or from about 50% to about 100% or from about 75% to about 100% or from about 90% to about 100%, using ASTM D6866-10, method B.

The topsheet may comprise a nonwoven topsheet; the backsheet may comprise one or more of a backsheet film or a backsheet nonwoven web; and the absorbent article may further comprise one or more of a landing zone, a stretch ear film, a back ear nonwoven web, tape tabs, ear hooks, a front ear nonwoven web, a waist feature nonwoven web, waist feature elastics, a barrier leg cuff nonwoven web, outer leg elastics, an acquisition material, a core cover nonwoven web, chassis adhesives, or core adhesives.

At least one of the nonwoven topsheet, the backsheet film, the backsheet nonwoven web, the landing zone, the stretch ear film, the back ear nonwoven web, the tape tabs, the ear hooks, the front ear nonwoven web, the waist feature nonwoven web, the waist feature elastics, the barrier leg cuff nonwoven web, the outer leg elastics, the acquisition material, the core cover nonwoven web, the chassis adhesives, or the core adhesives may comprise a bio-based polyolefin with a bio-based content from about 10% to about 100% using ASTM D6866-10, method B. At least one of the nonwoven topsheet, the backsheet film, the backsheet nonwoven web, the landing zone, the stretch ear film, the back ear nonwoven web, the tape tabs, the ear hooks, the front ear nonwoven web, the waist feature nonwoven web, the waist feature elastics, the barrier leg cuff nonwoven web, the outer leg elastics, the acquisition material, the core cover nonwoven web, the chassis adhesives, or the core adhesives may comprise at least about 50% by weight or at least about 75% by weight or at least 95% by weight of polyolefin. The at least one component that comprises at least about 50% by weight or at least about 75% by weight or at least about 95% by weight of polyolefin may comprise a bio-based polyolefin with a bio-based content from about 5% to about 100% using ASTM D6866-10, method B.

The absorbent article may further comprise an acquisition material that is positioned intermediate the topsheet and the absorbent core, in which the absorbent core is positioned intermediate the acquisition material and the backsheet.

The polyolefin may comprise one or more of low density polyethylene, high density polyethylene, linear low density polyethylene, a propylene homopolymer, an ethylene copolymer, or a propylene copolymer or one or more blends thereof.

In accordance with an aspect of the present disclosure, an absorbent article is provided comprising the following enumerated components: (1) a topsheet; (2) a backsheet film; (3) a backsheet nonwoven web; (4) a landing zone; (5) a stretch ear film; (6) a back ear nonwoven web; (7) tape tabs; (8) ear hooks; (9) a front ear nonwoven web; (10) a waist feature nonwoven web; (11) waist feature elastics; (12) a barrier leg cuff nonwoven web; (13) outer leg elastics; (14) an acquisition material; (15) a core cover nonwoven web; (16) chassis adhesives; and (17) core adhesives. The topsheet may be joined to a backsheet defined by the backsheet film and the backsheet nonwoven web. The core cover nonwoven web and a core absorbent material may be positioned intermediate the topsheet and the backsheet. At least 13 of the 17 enumerated components of the absorbent article may comprise one or more polyolefins. The core absorbent material may comprise superabsorbent polymers with a bio-based content from about 5% to about 100% using ASTM D6866-10, method B.

At least 14 or at least 15 or at least 16 of the 17 enumerated components of the absorbent article may comprise one or more polyolefins.

At least one or at least two or at least three or at least four or at least five of the 17 enumerated components that comprise one or more polyolefins may comprise a bio-based polyolefin with a bio-based content from about 5% to about 100% using ASTM D6866-10, method B.

At least one of the 17 enumerated components that comprises one or more polyolefins may comprise a bio-based polyolefin with a bio-based content from about 10% to about 100% or from about 25% to about 100% or from about 40% to about 100% or from about 50% to about 100% or from about 75% to about 100% or from about 90% to about 100%, using ASTM D6866-10, method B.

The bio-based content of the superabsorbent polymers may comprise from about 10% to about 100% or from about 25% to about 100% or from about 40% to about 100% or from about 50% to about 100% or from about 75% to about 100% or from about 90% to about 100%, using ASTM D6866-10, method B using ASTM D6866-10, method B.

In some examples, the core absorbent material may be substantially free of an absorbent pulp. In other examples, the core absorbent material may further comprise an absorbent pulp.

The core absorbent material may comprise at least about 60% by weight or at least about 70% by weight or at least about 90% by weight of the superabsorbent polymers.

At least one of the topsheet, the backsheet film, the backsheet nonwoven web, the landing zone, the stretch ear film, the back ear nonwoven web, the tape tabs, the ear hooks, the front ear nonwoven web, the waist feature nonwoven web, the waist feature elastics, the barrier leg cuff nonwoven web, the outer leg elastics, the acquisition material, the core cover nonwoven web, the chassis adhesives; or the core adhesives may comprise at least about 50% by weight or at least 75% by weight or at least about 95% by weight of polyolefin.

In accordance with an aspect of the present disclosure, an absorbent article is provided comprising the following enumerated components: (1) a topsheet; (2) a backsheet film; (3) a backsheet nonwoven web; (4) belt elastics; (5) a belt nonwoven web; (6) chassis adhesives; (7) a barrier leg cuff nonwoven web; (8) outer leg elastics; (9) an acquisition material; (10) a core cover nonwoven web; and (11) core adhesives. The topsheet may be joined to a backsheet defined by the backsheet film and the backsheet nonwoven web. The core cover nonwoven web and a core absorbent material may be positioned intermediate the topsheet and the backsheet. At least 7 of the 11 enumerated components of the absorbent article may comprise one or more polyolefins. The core absorbent material may comprise superabsorbent polymers with a bio-based content from about 5% to about 100% using ASTM D6866-10, method B.

At least 8 or at least 9 or at least 10 of the 11 enumerated components of the absorbent article may comprise one or more polyolefins.

At least one or at least two or at least three or at least four or at least five of the 11 enumerated components that comprise one or more polyolefins may comprise a bio-based polyolefin with a bio-based content from about 5% to about 100% using ASTM D6866-10, method B.

At least one of the enumerated components that comprises one or more polyolefins may comprise a bio-based polyolefin with a bio-based content from about 10% to about 100% or from about 25% to about 100% or from about 40% to about 100% or from about 50% to about 100% or from about 75% to about 100% or from about 90% to about 100%, using ASTM D6866-10, method B.

The bio-based content of the superabsorbent polymers may comprise from about 10% to about 100% or from about 25% to about 100% or from about 40% to about 100% or from about 50% to about 100% or from about 75% to about 100% or from about 90% to about 100%, using ASTM D6866-10, method B using ASTM D6866-10, method B.

In some examples, the core absorbent material may be substantially free of an absorbent pulp. In other examples, the core absorbent material may further comprise an absorbent pulp.

The core absorbent material may comprise at least about 60% by weight or at least 70% by weight or at least 90% by weight of the superabsorbent polymers.

At least one of the topsheet, the backsheet film, the backsheet nonwoven web, the belt elastics, the belt nonwoven web, the chassis adhesives, the barrier leg cuff nonwoven web, the outer leg elastics, the acquisition material, the core cover nonwoven web, or the core adhesives may comprise at least about 50% by weight or at least 75% by weight or at least 95% by weight of polyolefin.

In accordance with an aspect of the present disclosure, a package comprising a plurality of the absorbent articles according to the present disclosure is provided, in which the package has an In-Bag Stack Height of from about 70 mm to about 110 mm.

DETAILED DESCRIPTION

Definition of Terms

Figure 1:
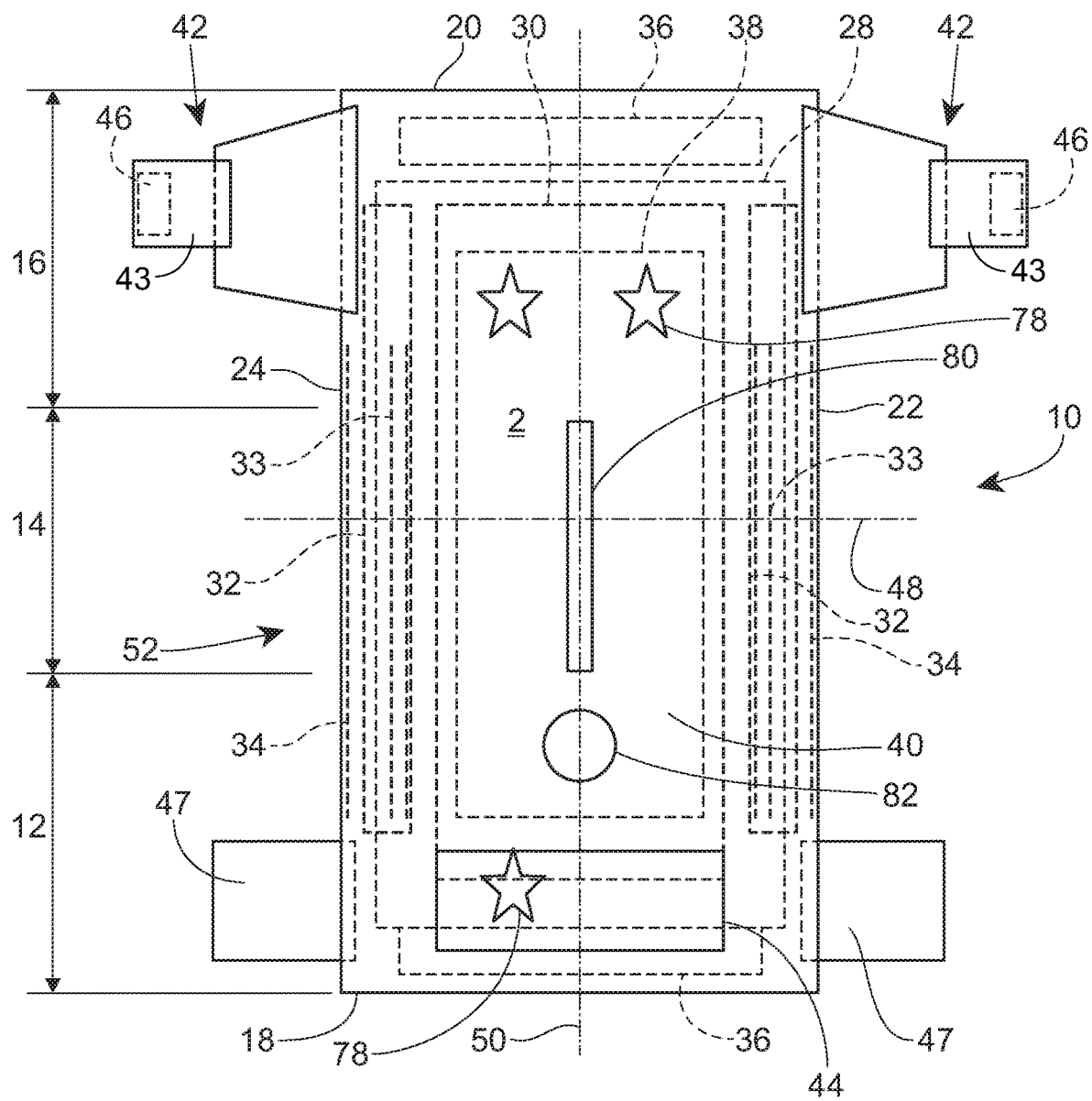
FIG. 1 is a plan view of an example absorbent article in the form of a taped diaper, garment-facing surface facing the viewer, in a flat laid-out state.

The term "absorbent article" may include disposable articles such as sanitary napkins, panty liners, tampons, interlabial devices, wound dressings, pants, taped diapers, adult incontinence articles, wipes, and the like. At least some of such absorbent articles are intended for the absorption of body liquids, such as menses or blood, vaginal discharges, urine, and feces. Wipes may be used to absorb body liquids, or may be used for other purposes, such as for cleaning surfaces. The nonwoven materials described herein may comprise at least part of other articles such as scouring pads, wet or dry-mop pads (such as SWIFFER® pads), paper towels, toilet tissue, and the like.

The term "bio-based" may be used herein to refer to a component of an absorbent article that can be produced or is derived from a renewable resource, as defined herein.

"Bio-based content" refers to the amount of carbon from a renewable resource in a material as a percent of the mass of the total organic carbon in the material, as determined by ASTM D6866-10, method B. In order to apply the methodology of ASTM D6866-10, method B, to determine the bio-based content of any absorbent article or component thereof, a sample may be ground into particulates less than about 20 mesh using known grinding methods (e.g., Wiley® mill (Thomas Scientific, LLC)), and a representative sample of suitable mass taken from the randomly mixed particles. Alternatively, if the sample is merely a layer of material, then the layer itself may be analyzed without the need for a pre-grinding step. Determining the bio-based content of a component of an absorbent would first require the component to be dissected, isolated, or cleanly removed from a completed absorbent article as the first step of the analysis. The bio-based content of a component material as described herein would be the mean value of representative sampling of the component as describe above from five different absorbent articles from a given package of absorbent articles or five absorbent articles from randomly purchased packages of a given absorbent article. Note that any carbon from inorganic sources, such as calcium carbonate, is not included in determining the bio-based content of the material. See additional information below for measuring bio-sourced content in polymers. Components of the absorbent articles described in this application may be at least partially comprised of bio-sourced content as described in the following published U.S. patent applications: U.S. Pat. Appl. Pub. Nos. 2007/0219521, 2011/0139658, 2011/0139657, 2011/0152812, 2011/0139662, and 2011/0139659.

The term "disposable" may be used herein to describe absorbent articles and other products which are not intended to be laundered or otherwise restored or reused as an absorbent article or product (i.e., they are intended to be discarded after use and, preferably, to be recycled, composted or otherwise disposed of in an environmentally compatible manner).

Absorbent articles of the present invention may be "devoid of" or "free of" particular undesirable materials, ingredients, or characteristics in some forms. "Devoid of," "free of," and the like, as those terms are used herein, may mean that the absorbent article does not have more than trace amounts of background levels of the material, ingredient, or characteristic following these qualifiers; the amount of the material or ingredient does not cause harm or irritation that consumers typically associate with the material or ingredient; or the material or ingredient was not added to the absorbent article intentionally. In some instances, "devoid of" and "free of" can mean there is no measurable amount of the material or ingredient. For example, the absorbent article in some forms contain no measurable amounts of chlorine—that is, the article is characterized as being totally chlorine free.

The terms "elastic," "elastomer," and "elastomeric" may be used herein to refer to any material that is able to extend to a strain of at least 50% without breaking or rupturing when subjected to a tensile force and is able to recover substantially to its original dimensions after the force has been removed.

The term "film" refers to a sheet-like material wherein the length and width of the material far exceed the thickness of the material. Typically, films have a thickness of about 0.5 mm or less.

The term "joined to" encompasses configurations in which an element is directly secured to another element by affixing the element directly to the other element; configurations in which the element is indirectly secured to the other element by affixing the element to intermediate member(s) which in turn are affixed to the other element; and configurations in which one element is integral with another element, i.e., one element is essentially part of the other element. The term "joined to" encompasses configurations in which an element is secured to another element at selected locations, as well as configurations in which an element is completely secured to another element across the entire surface of one of the elements. The term "joined to" includes any known manner in which elements may be secured including, but not limited to mechanical entanglement.

The term "machine direction" or "MD" may be used herein to refer to the direction of material flow through a manufacturing process. In addition, relative placement and movement of material can be described as flowing in the machine direction through a process from upstream in the process to downstream in the process. The term "cross direction" or "CD" may be used herein to refer to a direction that is generally perpendicular to the machine direction.

"Natural fibers" refers to elongated substances produced by plants and animals and includes animal-based fibers and plant-based fibers, as those categories are described herein. Natural fibers, as that term is used herein, include fibers harvested without any post-harvest treatment step, as well as those having a post-treatment step, such as, for example, washing, scouring, bleaching, etc.

"Naturally-derived" materials include materials that are partially chemically altered without petroleum components and that have been minimally processed such that they not be altered to such an extent that they are substantially less biodegradable or more toxic.

"Plant-based fibers," as that term is used herein, includes both harvested fibers and synthetic fibers that comprise bio-based content. Harvested plant-based fibers include cellulosic matter, such as wood pulp; seed hairs, such as cotton; stem (or bast) fibers, such as flax and hemp; leaf fibers, such as sisal; and husk fibers, such as coconut.

The term "recyclable" may be used herein to refer to a material (e.g., plastic, paper, etc.) that has the ability to enter into established recycling streams or be used in a recycling stream avoiding the normal fate of a disposable absorbent product, namely deposition in a landfill.

The term "renewable resource" may be used herein to refer to a natural resource that may be produced by a natural process at a rate comparable to its rate of consumption (e.g., within a 100 year time frame). The resource may be replenished naturally, or via engineered agricultural techniques. Non-limiting examples of renewable resources may include plants, animals, fish, bacteria, fungi, and forestry products. These resources may be naturally occurring, hybrids, or genetically engineered organisms. Natural resources such as crude oil, coal, and peat that take longer than 100 years to form are generally not considered to be renewable resources.

The term "web" is used herein to refer to a material whose primary dimension is X-Y, i.e., along its length (or longitudinal direction) and width (or transverse direction). It should be understood that the term "web" is not necessarily limited to single layers or sheets of material. Thus, the web may comprise laminates or combinations of several sheets of the requisite type of materials.

Validation of Polymers Derived from Renewable Resources

A suitable validation technique is through $^{14}C$ analysis. A small amount of the carbon dioxide in the atmosphere is radioactive. This $^{14}C$ carbon dioxide is created when nitrogen is struck by an ultra-violet light produced neutron, causing the nitrogen to lose a proton and form carbon of molecular weight 14, which is immediately oxidized to carbon dioxide. This radioactive isotope represents a small but measurable fraction of atmospheric carbon. Atmospheric carbon dioxide is cycled by green plants to make organic molecules during photosynthesis. The cycle is completed when the green plants or other forms of life metabolize the organic molecules, thereby producing carbon dioxide that is released back to the atmosphere. Virtually all forms of life on Earth depend on this green plant production of organic molecules to grow and reproduce. Therefore, the $^{14}C$ that exists in the atmosphere becomes part of all life forms and their biological products. In contrast, fossil fuel-based carbon does not have the signature radiocarbon ratio of atmospheric carbon dioxide.

Assessment of the renewably-based carbon in a material may be performed through standard test methods. Using radiocarbon and isotope ratio mass spectrometry analysis, the bio-based content of materials may be determined. ASTM International, formally known as the American Society for Testing and Materials, has established a standard method for assessing the bio-based content of materials. The ASTM method is designated ASTM D6866-10, method B.

The application of ASTM D6866-10, method B, to derive a "bio-based content" is built on the same concepts as radiocarbon dating, but without use of the age equations. The analysis is performed by deriving a ratio of the amount of organic radiocarbon ($^{14}C$) in an unknown sample to that of a modern reference standard. The ratio is reported as a percentage with the units "pMC" (percent modern carbon).

The modern reference standard used in radiocarbon dating is a NIST (National Institute of Standards and Technology) standard with a known radiocarbon content equivalent approximately to the year AD 1950. AD 1950 was chosen since it represented a time prior to thermo-nuclear weapons testing, which introduced large amounts of excess radiocarbon into the atmosphere with each explosion (termed "bomb carbon"). The AD 1950 reference represents 100 pMC.

"Bomb carbon" in the atmosphere reached almost twice normal levels in 1963 at the peak of testing and prior to the treaty halting the testing. Its distribution within the atmosphere has been approximated since its appearance, showing values that are greater than 100 pMC for plants and animals living since AD 1950. It has gradually decreased over time with today's value being near 107.5 pMC. This means that a fresh biomass material such as corn could give a radiocarbon signature near 107.5 pMC.

Combining fossil carbon with present day carbon into a material will result in a dilution of the present day pMC content. By presuming 107.5 pMC represents present day biomass materials and 0 pMC represents petroleum derivatives, the measured pMC value for that material will reflect the proportions of the two component types. A material derived 100% from present day soybeans would give a radiocarbon signature near 107.5 pMC. If that material was diluted with 50% petroleum derivatives, for example, it would give a radiocarbon signature near 54 pMC (assuming the petroleum derivatives have the same percentage of carbon as the soybeans).

A bio-based content result is derived by assigning 100% equal to 107.5 pMC and 0% equal to 0 pMC. In this regard, a sample measuring 99 pMC will give an equivalent bio-based content value of 92%.

Assessment of the materials described herein may be done in accordance with ASTM D6866-10, method B. The mean values quoted in a report from this type of analysis encompass an absolute range of 6% (plus and minus 3% on either side of the bio-based content value) to account for variations in end-component radiocarbon signatures. It is presumed that all materials are present day or fossil in origin and that the bio-based content result is the amount of bio-based component "present" in the material. One company providing reports on or performing bio-based content analysis of a component of an absorbent article according to ASTM D6866-10, method B is Beta Analytic Inc. of Miami, Fla.

General Description of an Absorbent Article

Figure 2:
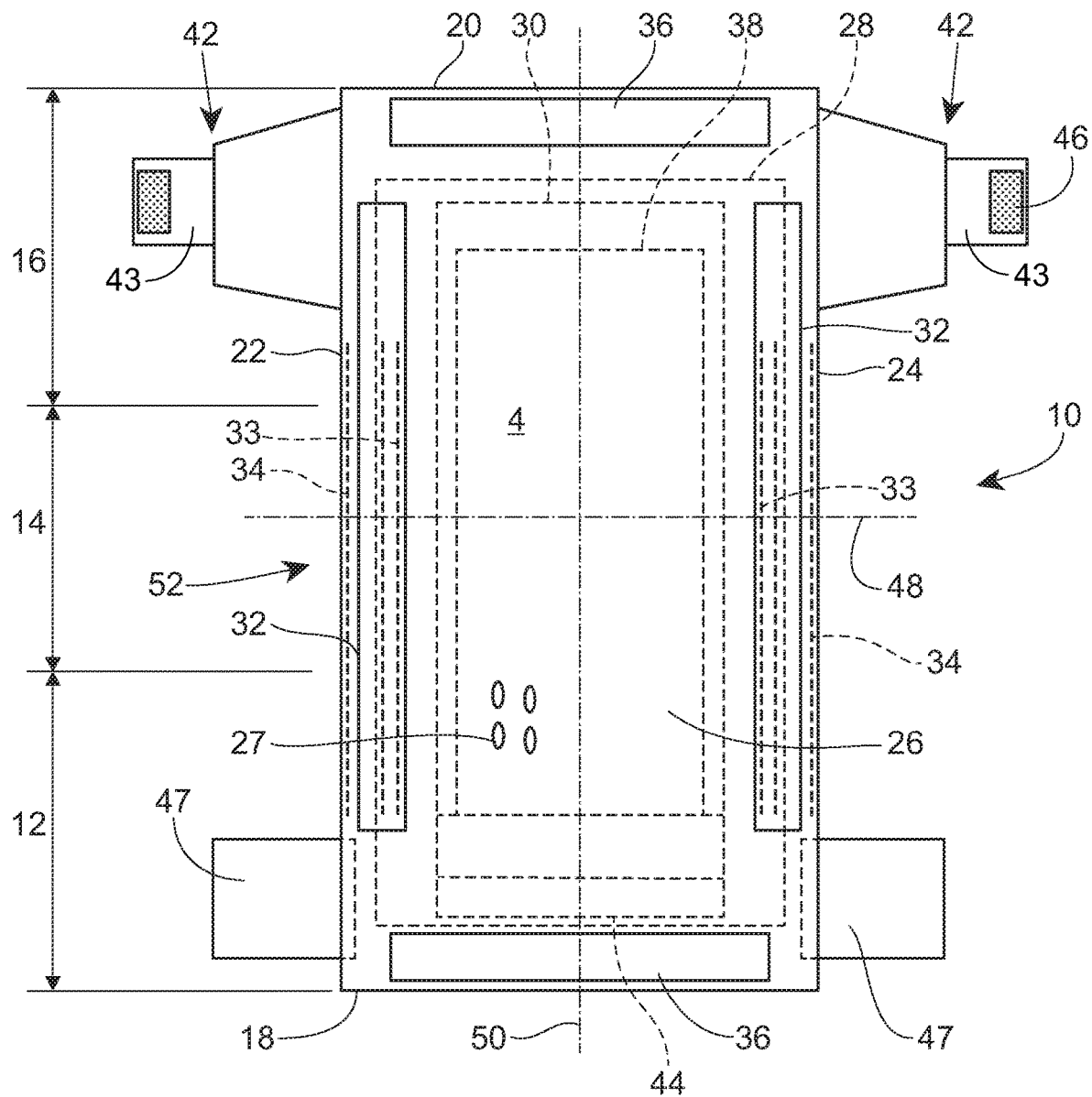
FIG. 2 is a plan view of the example absorbent article of FIG. 1, wearer-facing surface facing the viewer, in a flat laid-out state.
Figure 3:
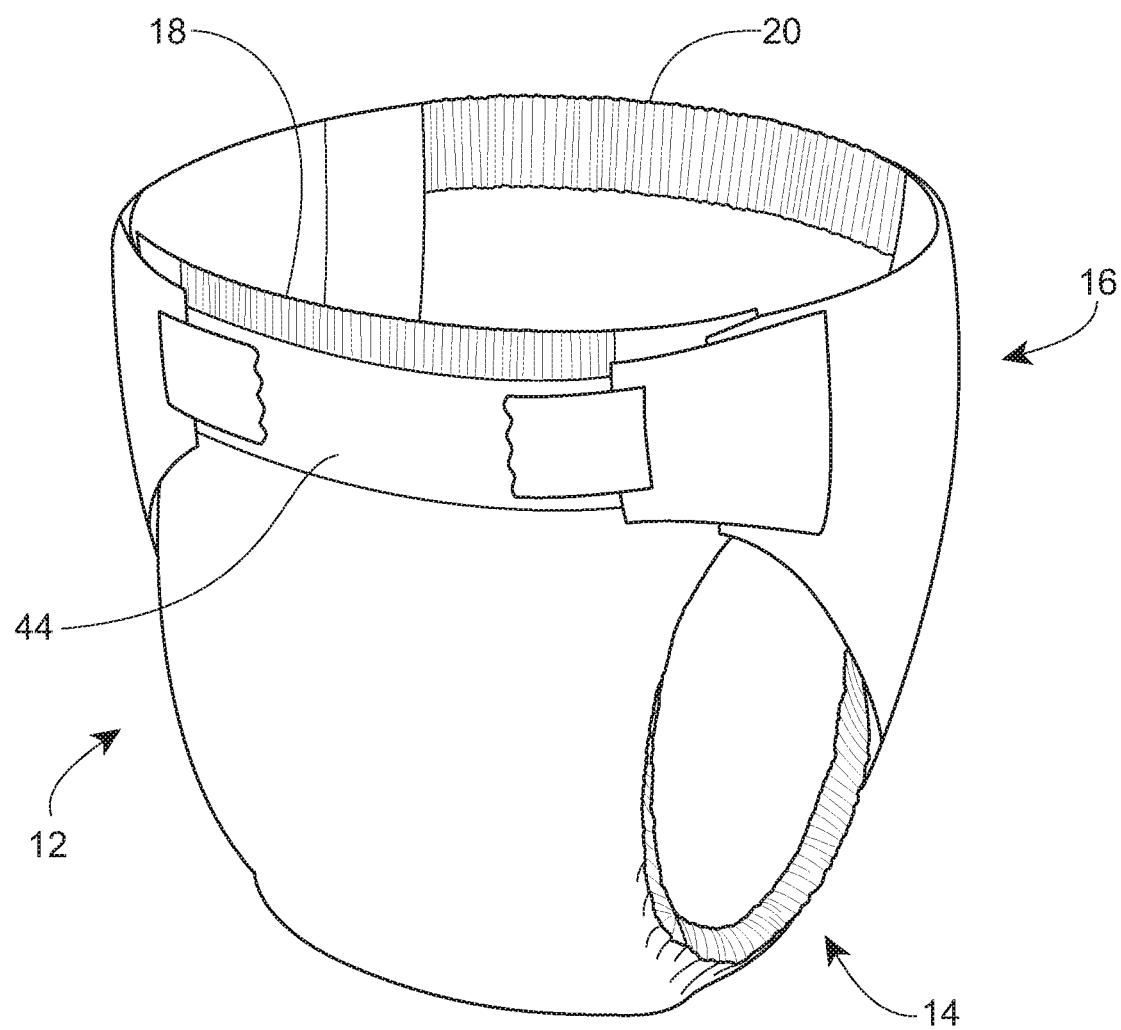
FIG. 3 is a front perspective view of the absorbent article of FIGS. 1 and 2 in a fastened position.

An example absorbent article 10 according to the present disclosure, shown in the form of a taped diaper, is represented in FIGS. 1-3. FIG. 1 is a plan view of the example absorbent article 10, garment-facing surface 2 facing the viewer in a flat, laid-out state (i.e., no elastic contraction). FIG. 2 is a plan view of the example absorbent article 10 of FIG. 1, wearer-facing surface 4 facing the viewer in a flat, laid-out state. FIG. 3 is a front perspective view of the absorbent article 10 of FIGS. 1 and 2 in a fastened configuration. The absorbent article 10 of FIGS. 1-3 is shown for illustration purposes only, as the present disclosure may be used for making a wide variety of diapers, including adult incontinence products, pants, or other absorbent articles, such as sanitary napkins and absorbent pads, for example.

The absorbent article 10 may comprise a front waist region 12, a crotch region 14, and a back waist region 16. The crotch region 14 may extend intermediate the front waist region 12 and the back waist region 16. The front waist region 12, the crotch region 14, and the back waist region 16 may each be ⅓ of the length of the absorbent article 10. The absorbent article 10 may comprise a front end edge 18, a back end edge 20 opposite to the front end edge 18, and longitudinally extending, transversely opposed side edges 22 and 24 defined by the chassis 52.

The absorbent article 10 may comprise a liquid permeable topsheet 26, a liquid impermeable backsheet 28, and an absorbent core 30 positioned at least partially intermediate the topsheet 26 and the backsheet 28. The absorbent article 10 may also comprise one or more pairs of barrier leg cuffs 32 with or without elastics 33, one or more pairs of outer leg elastics 34, one or more elastic waistbands 36, and/or one or more acquisition materials 38. The acquisition material or materials 38 may be positioned intermediate the topsheet 26 and the absorbent core 30. An outer cover material 40, such as a nonwoven material, may cover a garment-facing side of the backsheet 28. The absorbent article 10 may comprise back ears 42 in the back waist region 16. The back ears 42 may comprise fasteners 46 and may extend from the back waist region 16 of the absorbent article 10 and attach (using the fasteners 46) to the landing zone area or landing zone material 44 on a garment-facing portion of the front waist region 12 of the absorbent article 10. The absorbent article 10 may also have front ears 47 in the front waist region 12. The absorbent article 10 may have a central lateral (or transverse) axis 48 and a central longitudinal axis 50. The central lateral axis 48 extends perpendicular to the central longitudinal axis 50.

Figure 4:
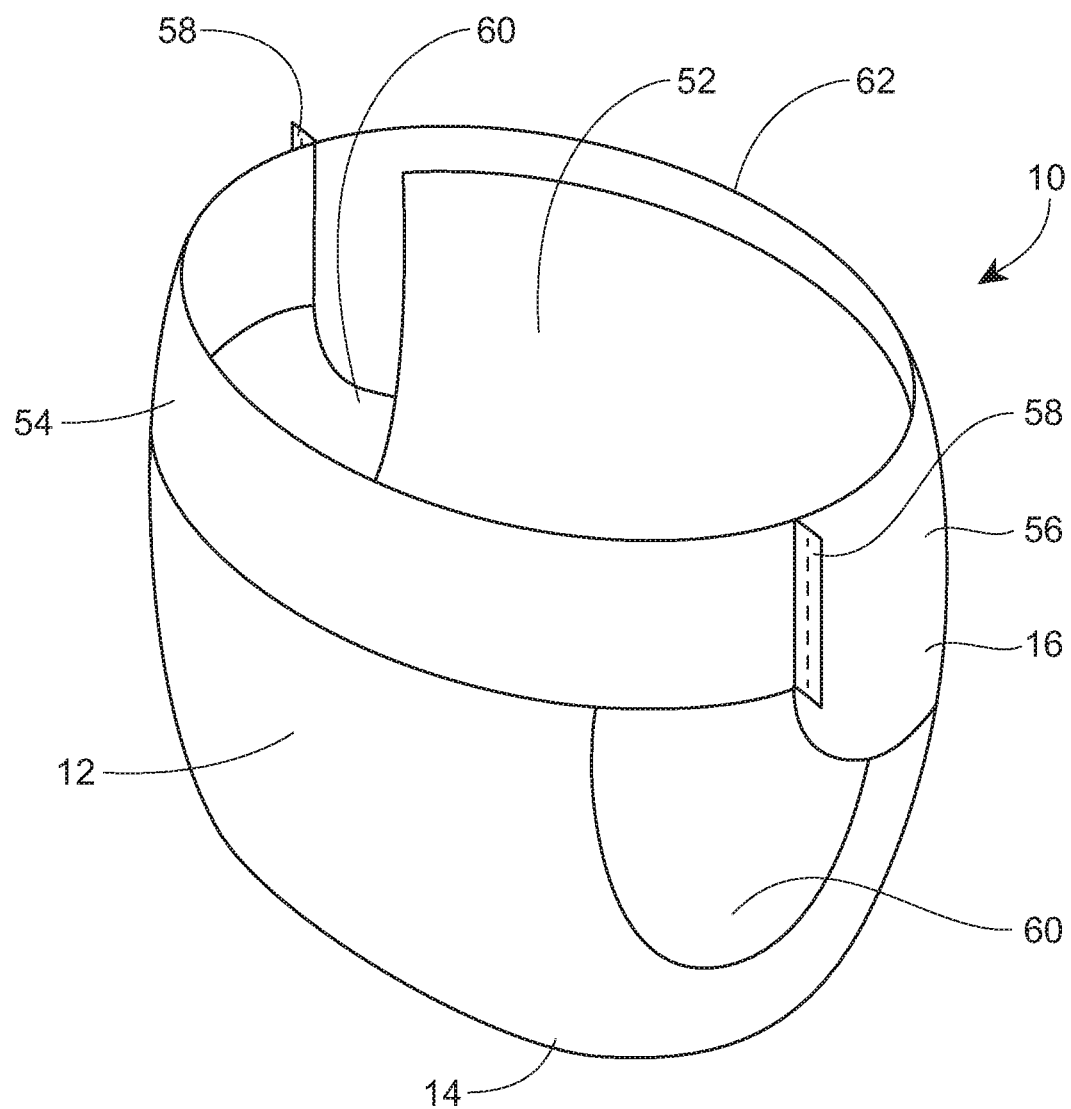
FIG. 4 is a front perspective view of an absorbent article in the form of a pant.
Figure 5:
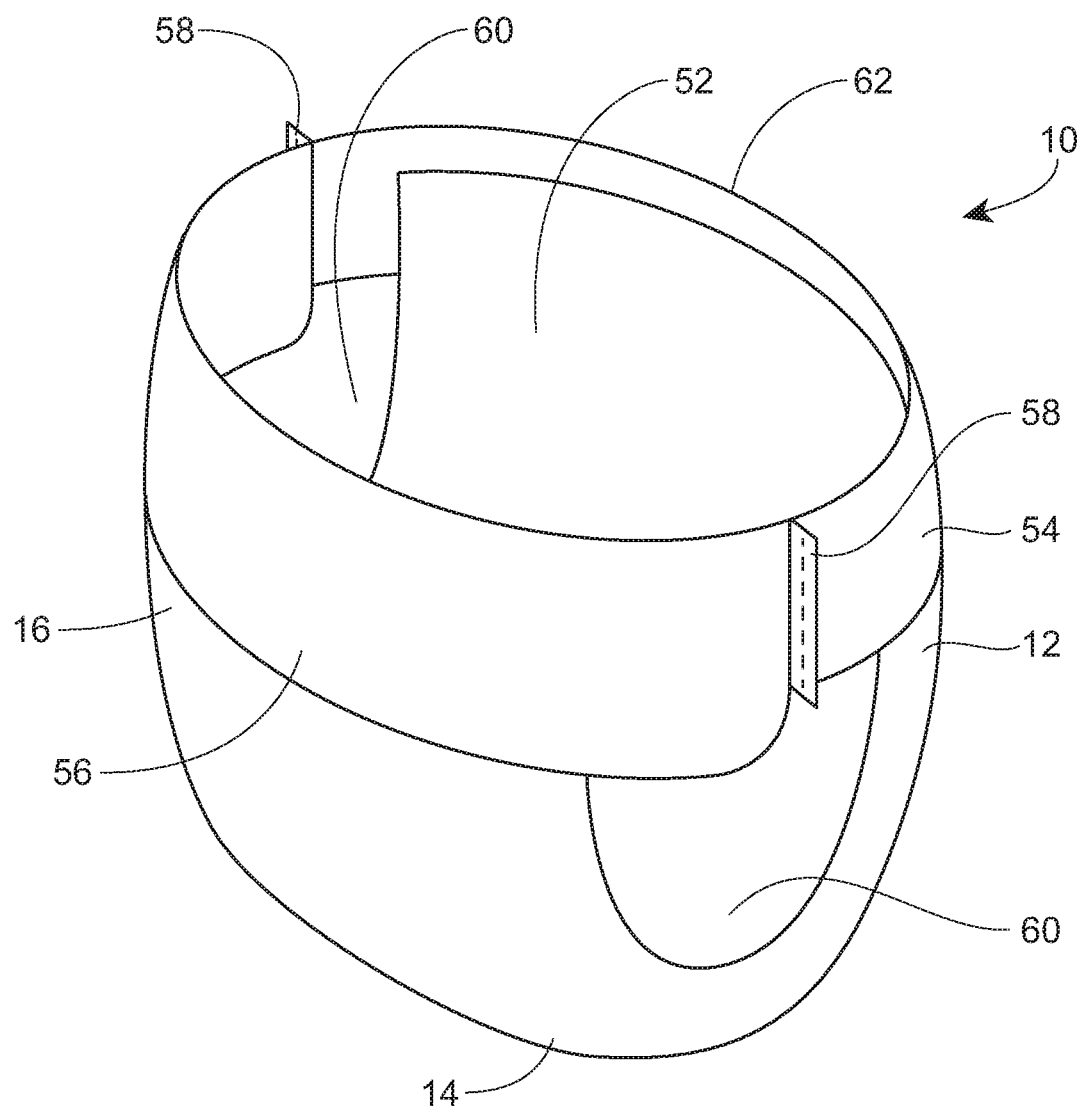
FIG. 5 is a rear perspective view of the absorbent article of FIG. 4.
Figure 6:
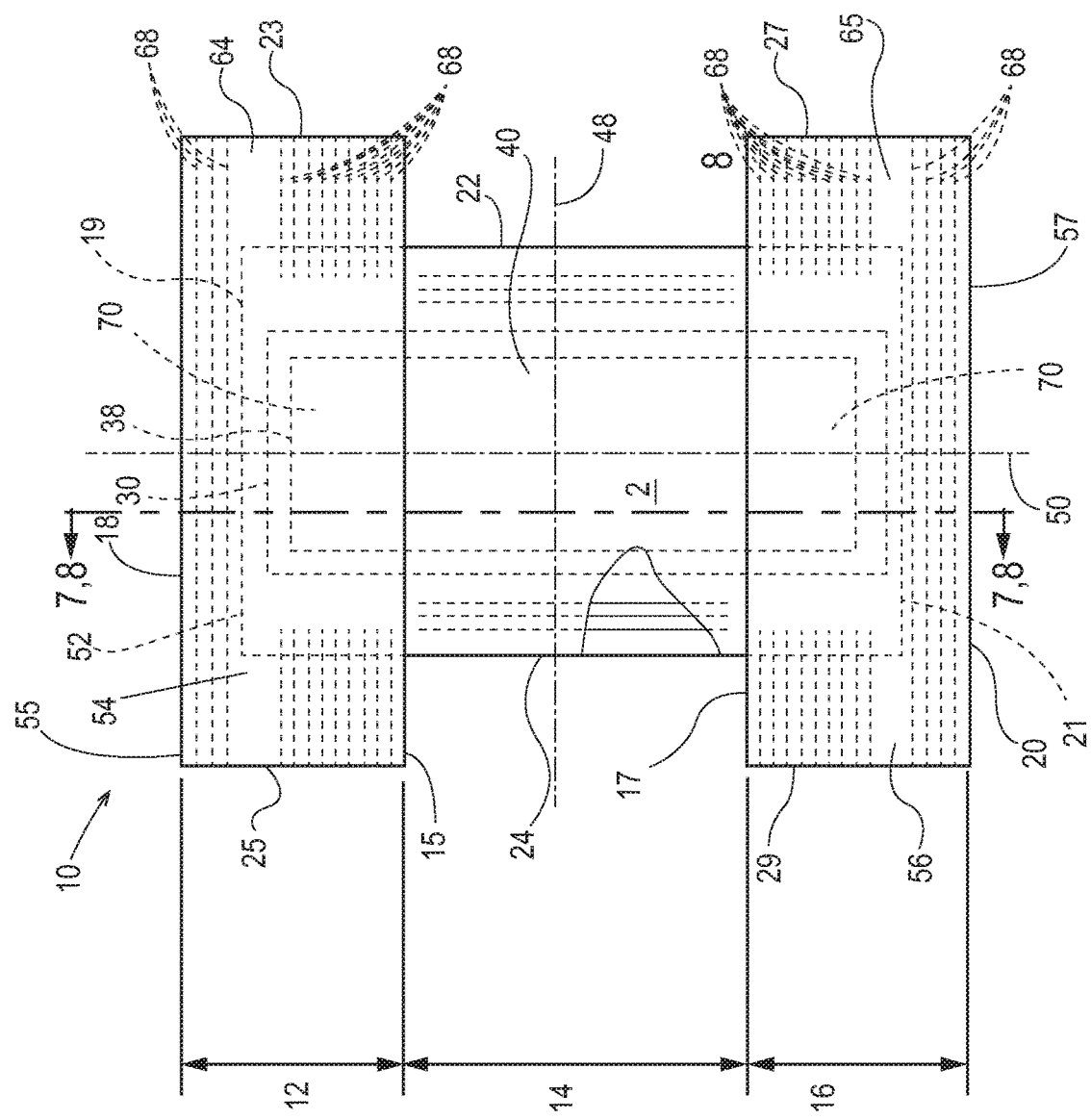
FIG. 6 is a plan view of the absorbent article of FIG. 4, laid flat, with a garment-facing surface facing the viewer.
Figure 7:
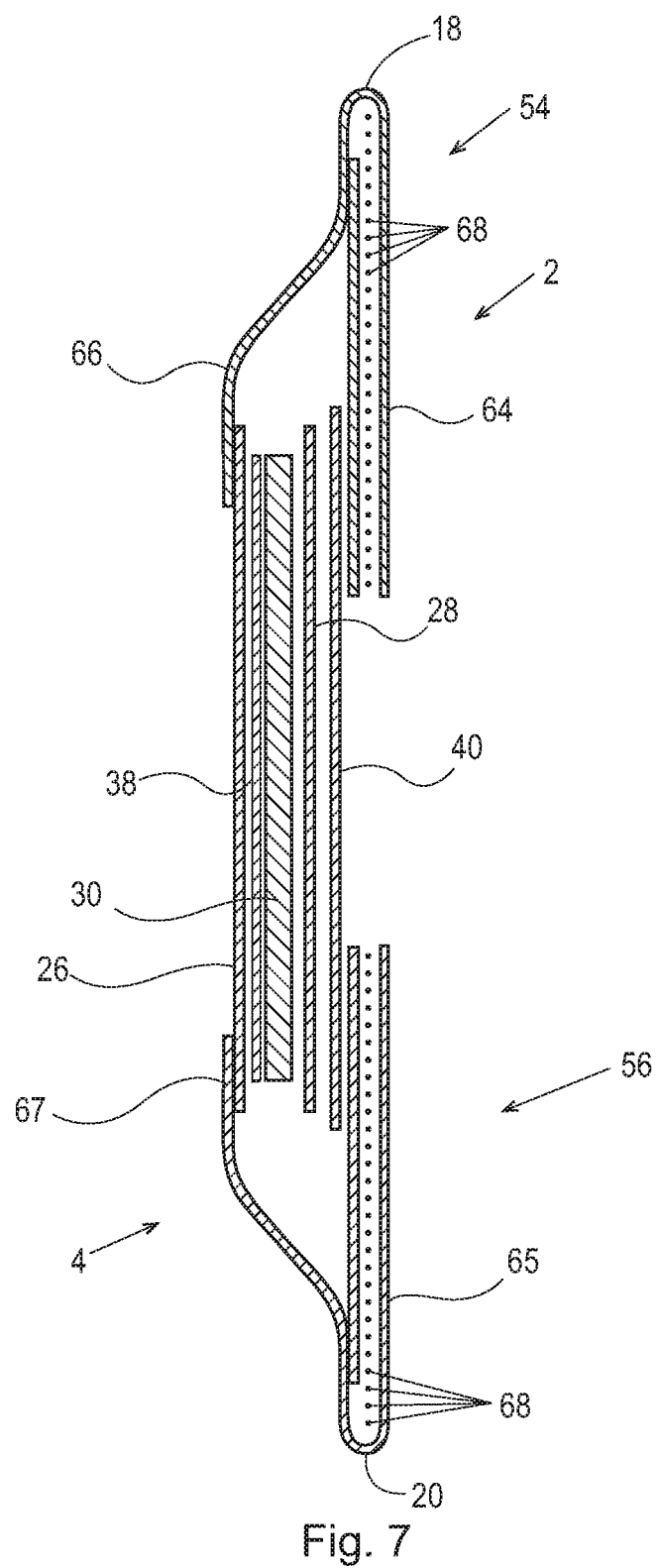
FIG. 7 is a cross-sectional view of the absorbent article taken about line 7-7 of FIG. 6.
Figure 8:
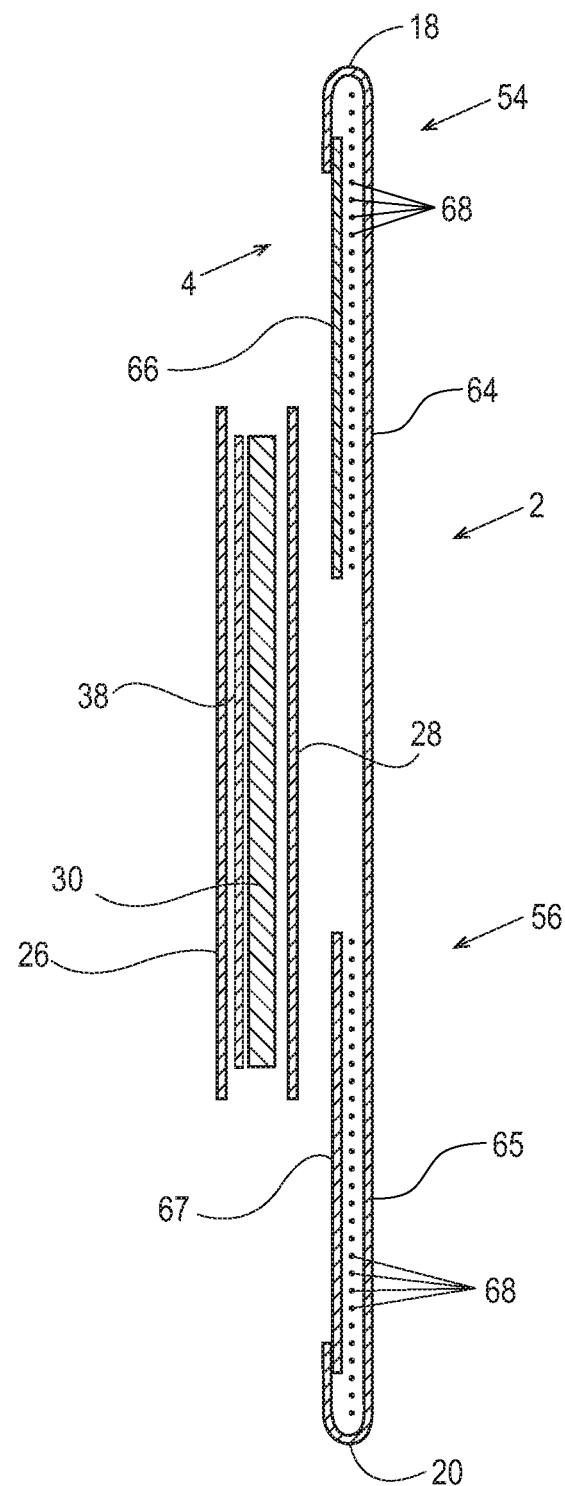
FIG. 8 is a cross-sectional view of the absorbent article taken about line 8-8 of FIG. 6.

In other instances, the absorbent article may be in the form of a pant having permanent or refastenable side seams. Suitable refastenable seams are disclosed in U.S. Pat. Appl. Pub. No. 2014/0005020 and U.S. Pat. No. 9,421,137. Referring to FIGS. 4-8, an example absorbent article 10 in the form of a pant is illustrated. FIG. 4 is a front perspective view of the absorbent article 10. FIG. 5 is a rear perspective view of the absorbent article 10. FIG. 6 is a plan view of the absorbent article 10, laid flat, with the garment-facing surface facing the viewer. Elements of FIGS. 4-8 having the same reference number as described above with respect to FIGS. 1-3 may be the same element (e.g., absorbent core 30). FIG. 7 is an example cross-sectional view of the absorbent article taken about line 7-7 of FIG. 6. FIG. 8 is an example cross-sectional view of the absorbent article taken about line 8-8 of FIG. 6. FIGS. 7 and 8 illustrate example forms of front and back belts 54, 56.

The absorbent article 10 may have a front waist region 12, a crotch region 14, and a back waist region 16. Each of the regions 12, 14, and 16 may be ⅓ of the length of the absorbent article 10. The absorbent article 10 may have a chassis 52 (sometimes referred to as a central chassis or central panel) comprising a topsheet 26, a backsheet 28, and an absorbent core 30 disposed at least partially intermediate the topsheet 26 and the backsheet 28, and an optional acquisition material 38, similar to that as described above with respect to FIGS. 1-3. The absorbent article 10 may comprise a front belt 54 in the front waist region 12 and a back belt 56 in the back waist region 16. The chassis 52 may be joined to a wearer-facing surface 4 of the front and back belts 54, 56 or to a garment-facing surface 2 of the belts 54, 56 via one or more chassis glues or adhesives and/or one or more non-adhesive methods as described herein. Side edges 23 and 25 of the front belt 54 may be joined to side edges 27 and 29, respectively, of the back belt 56 to form two side seams 58. The side seams 58 may be any suitable seams known to those of skill in the art, such as butt seams or overlap seams, for example. When the side seams 58 are permanently formed or refastenably closed, the absorbent article 10 in the form of a pant has two leg openings 60 and a waist opening circumference 62. The side seams 58 may be permanently joined using adhesives or bonds, for example, or may be refastenably closed using hook and loop fasteners, for example.

Belts

Referring to FIGS. 7 and 8, the front and back belts 54 and 56 may comprise front and back inner belt layers 66 and 67 and front and back outer belt layers 64 and 65 having an elastomeric material (e.g., strands 68 or a film (which may be apertured)) disposed at least partially therebetween. The elastic elements 68 or the film may be relaxed (including being cut) to reduce elastic strain over the absorbent core 30 or, may alternatively, run continuously across the absorbent core 30. The elastics elements 68 may have uniform or variable spacing therebetween in any portion of the belts 54, 56. The elastic elements 68 may also be pre-strained the same amount or different amounts. The front and/or back belts 54 and 56 may have one or more elastic element free zones 70 where the chassis 52 overlaps the belts 54, 56. In other instances, at least some of the elastic elements 68 may extend continuously across the chassis 52.

The front and back inner belt layers 66, 67 and the front and back outer belt layers 64, 65 may be joined using adhesives, heat bonds, pressure bonds or thermoplastic bonds. Various suitable belt layer configurations can be found in U.S. Pat. Appl. Pub. No. 2013/0211363.

Front and back belt end edges 55 and 57 may extend longitudinally beyond the front and back chassis end edges 19 and 21 (as shown in FIG. 6) or they may be co-terminus. The front and back belt side edges 23, 25, 27, and 29 may extend laterally beyond the chassis side edges 22 and 24. The front and back belts 54 and 56 may be continuous (i.e., having at least one layer that is continuous) from belt side edge to belt side edge (e.g., the transverse distances from 23 to 25 and from 27 to 29). Alternatively, the front and back belts 54 and 56 may be discontinuous from belt side edge to belt side edge (e.g., the transverse distances from 23 to 25 and 27 to 29), such that they are discrete.

As disclosed in U.S. Pat. No. 7,901,393, the longitudinal length (along the central longitudinal axis 50) of the back belt 56 may be greater than the longitudinal length of the front belt 54, and this may be particularly useful for increased buttocks coverage when the back belt 56 has a greater longitudinal length versus the front belt 54 adjacent to or immediately adjacent to the side seams 58.

The front outer belt layer 64 and the back outer belt layer 65 may be separated from each other, such that the layers are discrete or, alternatively, these layers may be continuous, such that a layer runs continuously from the front belt end edge 55 to the back belt end edge 57. This may also be true for the front and back inner belt layers 66 and 67—that is, they may also be longitudinally discrete or continuous. Further, the front and back outer belt layers 64 and 65 may be longitudinally continuous while the front and back inner belt layers 66 and 67 are longitudinally discrete, such that a gap is formed between them—a gap between the front and back inner and outer belt layers 64, 65, 66, and 67 is shown in FIG. 7 and a gap between the front and back inner belt layers 66 and 67 is shown in FIG. 8.

The front and back belts 54 and 56 may include slits, holes, and/or perforations providing increased breathability, softness, and a garment-like texture. Underwear-like appearance can be enhanced by substantially aligning the waist and leg edges at the side seams 58 (see FIGS. 4 and 5).

The front and back belts 54 and 56 may comprise graphics (see e.g., 78 of FIG. 1). The graphics may extend substantially around the entire circumference of the absorbent article 10 and may be disposed across side seams 58 and/or across proximal front and back belt seams 15 and 17; or, alternatively, adjacent to the seams 58, 15, and 17 in the manner described in U.S. Pat. No. 9,498,389 to create a more underwear-like article. The graphics may also be discontinuous.

Alternatively, instead of attaching belts 54 and 56 to the chassis 52 to form a pant, discrete side panels may be attached to side edges of the chassis 22 and 24. Suitable forms of pants comprising discrete side panels are disclosed in U.S. Pat. Nos. 6,645,190; 8,747,379; 8,372,052; 8,361, 048; 6,761,711; 6,817,994; 8,007,485; 7,862,550; 6,969, 377; 7,497,851; 6,849,067; 6,893,426; 6,953,452; 6,840, 928; 8,579,876; 7,682,349; 7,156,833; and 7,201,744.

Top Sheet

The topsheet 26 is the outermost layer or component of the absorbent article 10 that is in contact with the wearer's skin. The topsheet 26 may be joined to portions of the backsheet 28, the absorbent core 30, the barrier leg cuffs 32, and/or any other layers as is known to those of ordinary skill in the art. The topsheet 26 may be compliant, soft-feeling, and non-irritating to the wearer's skin. Further, at least a portion of, or all of, the topsheet 26 may be liquid permeable, permitting liquid bodily exudates to readily penetrate through its thickness. A suitable topsheet may be manufactured from a wide range of materials, such as porous foams, reticulated foams, apertured plastic films, woven materials, nonwoven materials, woven or nonwoven materials of natural fibers (e.g., wood or cotton fibers), synthetic fibers or filaments (e.g., a polyester or a polyolefin, such as polyethylene (PE), polypropylene (PP), or bicomponent PE/PP fibers or mixtures thereof), or a combination of natural and synthetic fibers.

In one form of the present disclosure, the topsheet 26 may be a nonwoven material having one or multiple formed layers, nonwovens, or components comprising plant-based fibers other than wood pulp. The nonwoven may be made through well-known techniques; for example, the nonwoven may be a spunbond, a carded and air-through, hydroentangled, or calendar bonded nonwoven. The plant-based fibers may also be spun fibers made at least in part from bio-based materials. For example, the plant-based fibers may be spun poly lactic acid (PLA) fibers or bio-based polyolefin spun fibers. The plant-based fibers may be single component fibers or multi-component fibers, in which less than all of the components are plant-based fibers. One example is a bi-component fiber comprising a polyester core component and a bio-based polyethylene sheath component.

The topsheet 26 may have one or more layers. The topsheet 26 may be apertured (FIG. 2, element 27), may have any suitable three-dimensional features, and/or may have a plurality of embossments (e.g., a bond pattern). The topsheet 26 may be apertured by overbonding a material and then rupturing the overbonds through ring rolling, such as disclosed in U.S. Pat. No. 5,628,097 and disclosed in U.S. Pat. Appl. Pub. No. 2016/0136014. The topsheet 26 may be hydrophilic or hydrophobic or may have hydrophilic and/or hydrophobic portions or layers. If the topsheet 26 is hydrophobic, typically apertures will be present so that bodily exudates may pass through the topsheet 26. The topsheet 26 may have a basis weight of from about 10 gsm to about 40 gsm.

In one form, the topsheet 26 may be a dual layer, spunbond nonwoven web. Each of the layers may have a basis weight from about 10 gsm to about 25 gsm or 35 gsm. One layer may have similar or different hydrophilicity/hydrophobicity profiles compared to the other layer. In another form, the topsheet 26 may be an air through carded nonwoven web comprising a blend (e.g., 50-50 weight percent) of polyester fibers and bio-based polyethylene fibers. The basis weight of such a nonwoven is typically less than about 20 gsm, 25 gsm, 35 gsm, or 40 gsm.

Many commercially-available absorbent articles comprise a skin care composition on at least a portion of the topsheet 26. These compositions tend to contain petrolatum or other petroleum-based materials as their main component. In some forms of the present invention, the topsheet is devoid of a lotion or skin care composition. However, a skin care composition or lotion may optionally be added to the topsheet 26, and if so, it is preferred, but not required, to employ a composition based upon natural or naturally-derived materials such as fats, oils, or waxes, for example. The optional lotions may comprise vegetable oils, algae oils, bacterial-derived oils, and animal fats, combinations of these, and the like. Representative examples of vegetable oils include argan oil, canola oil, rapeseed oil, coconut oil, corn oil, cottonseed oil, olive oil, palm oil, peanut oil, safflower oil, sesame oil, soybean oil, sunflower oil, high oleoyl soybean oil, high oleoyl sunflower oil, linseed oil, palm kernel oil, tung oil, castor oil, high erucic rape oils, Jatropha oil, combinations of these, and the like. Representative examples of animal fats include lard, tallow, chicken fat, yellow grease, fish oil, combinations of these, and the like. A representative example of a synthesized oil includes tall oil, which is a byproduct of wood pulp manufacture. Additional suitable lotion compositions derived from renewable resources are disclosed in U.S. Pat. Appl. Pub. No. 2013/0144239.

Backsheet

The backsheet 28 is generally that portion of the absorbent article 10 positioned proximate to the garment-facing surface of the absorbent core 30. The backsheet 28 may be joined to portions of the topsheet 26, the outer cover material 40, the absorbent core 30, and/or any other layers of the absorbent article by any attachment methods known to those of skill in the art. The backsheet 28 prevents, or at least inhibits, the bodily exudates absorbed and contained in the absorbent core 10 from soiling articles such as bedsheets, undergarments, and/or clothing. The backsheet 28 is typically liquid impermeable, or at least substantially liquid impermeable. The backsheet 28 may, for example, be or comprise a thin plastic backsheet film, such as a thermoplastic film having a thickness of about 0.012 mm to about 0.051 mm. Other suitable backsheet materials may include breathable materials or additives as described herein (e.g. calcium carbonate particles) inducing microporous zones in the backsheet film, which permit vapors to escape from the absorbent article 10, while still preventing, or at least inhibiting, bodily exudates from passing through the backsheet. Backsheet films may optionally comprise bio-based materials, such as, for example, bio-based polyethylene, bio-based polypropylene, or other bio-based polyolefins.

Outer Cover Material

The outer cover material 40 (sometimes referred to as a backsheet nonwoven web) may comprise one or more nonwoven materials joined to the backsheet 28 and that covers the backsheet 28. The outer cover material 40 is typically the layer facing outward—i.e., towards garments or undergarments, when present, and away from the wearer's skin. A caregiver interacts significantly with the outer cover material 40 when holding/comforting the wearer and/or changing the absorbent article 10. The outer cover material 40 forms at least a portion of the garment-facing surface 2 of the absorbent article 10 and effectively "covers" the backsheet 28 so that film is not present on the garment-facing surface 2. The outer cover material 40 may comprise a bond pattern, apertures, and/or three-dimensional features.

In one form, the outer cover material 40 may be a carded nonwoven or a multi-layered nonwoven comprising carded layers and one or more spunbond layers. The outer cover nonwoven may comprise a combination of plant-based fibers and synthetic fibers that are not plant-based. For example, the nonwoven may comprise both polypropylene fibers and cotton fibers; see, for example, U.S. Pat. Appl. Pub. No. 2017/0203542. The cotton content may range from about 3%, 5%, 10%, or 15% to about 50%, by weight of the nonwoven. When synthetic fibers such as polypropylene are employed, it is preferred that the polypropylene be non-phthalate catalyst polypropylene fibers. Furthermore, the polypropylene fibers may comprise bio-based polyethylene, bio-based polypropylene, or other bio-based polyolefins where such bio-based polyolefin is also phthalate free.

In another form, the outer cover material 40 may comprise a hydroentangled, dual layer nonwoven web, in which one layer comprises a polypropylene spunbond web having a basis weight in the range of from about 5 to 15 gsm and the other layer comprises a carded nonwoven web comprising cotton fibers and a basis weight in the range of from about 10 to about 25 gsm. In a further form, the outer cover material 40 may comprise an air through carded nonwoven web comprising a blend of polypropylene fibers and cotton fibers. The cotton fibers may be included in these nonwoven webs in an amount of about greater than or less than 5%, 10%, or 15% to about 20%, 30%, or 50%, by weight of the overall nonwoven web.

Absorbent Core

Figure 9:
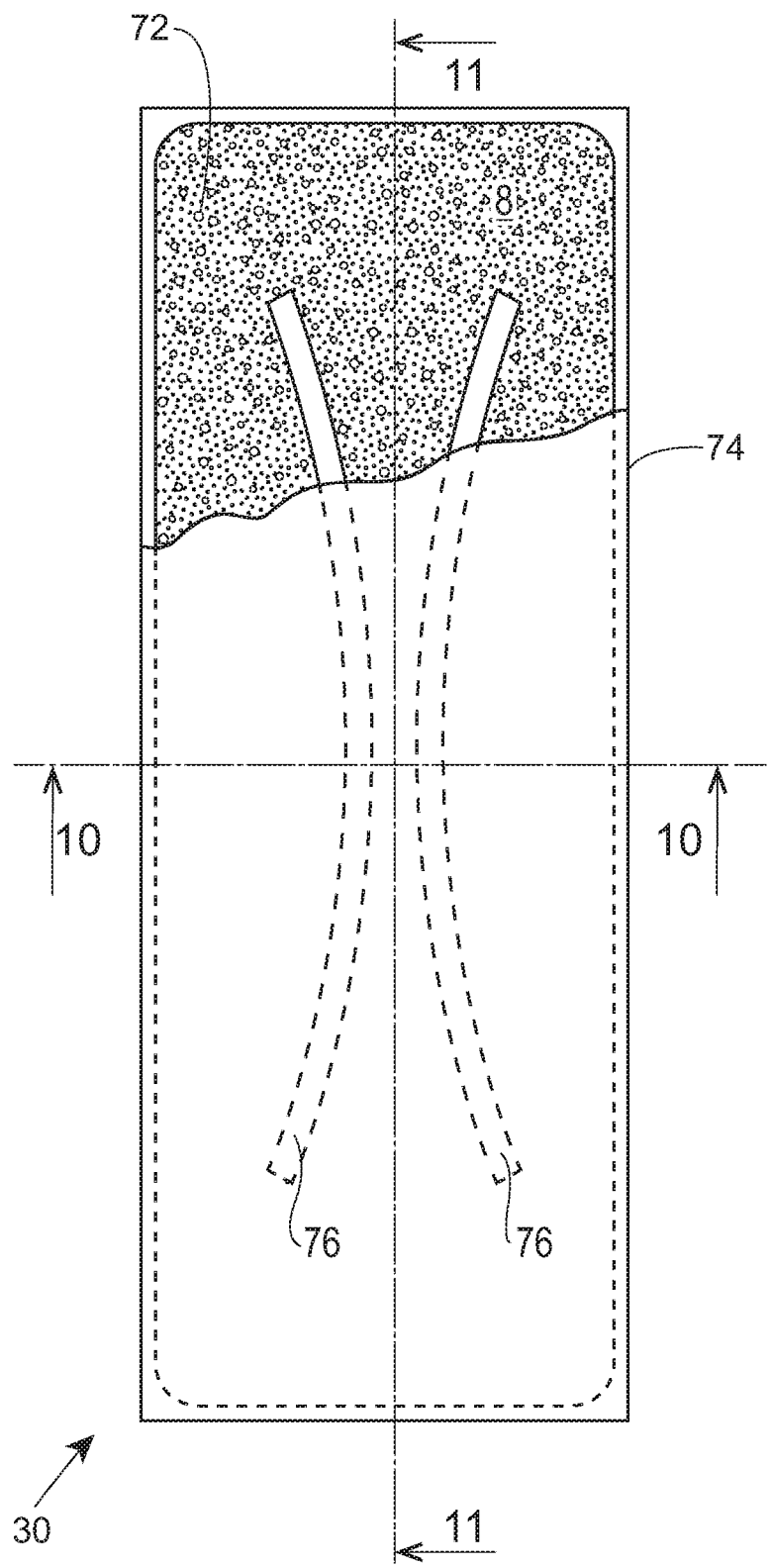
FIG. 9 is a plan view of an example absorbent core or an absorbent article.
Figure 10:
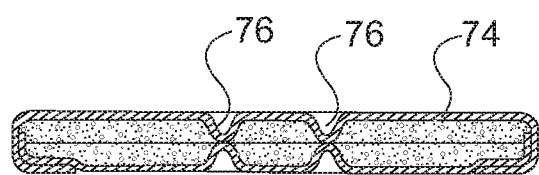
FIG. 10 is a cross-sectional view, taken about line 10-10, of the absorbent core of FIG. 9.
Figure 11:
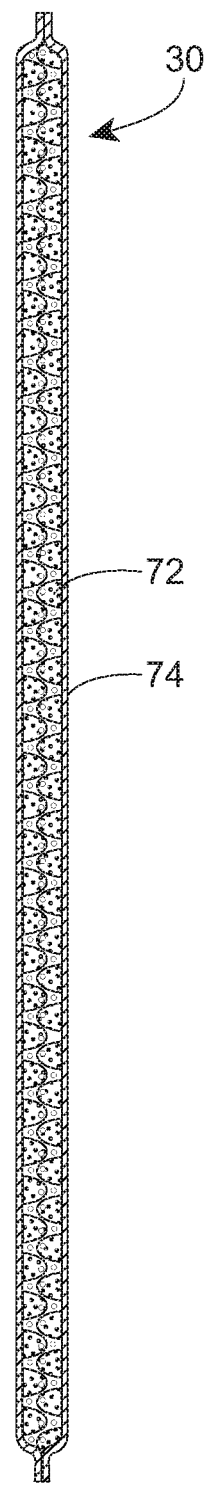
FIG. 11 is a cross-sectional view, taken about line 11-11, of the absorbent core of FIG. 10.

As used herein, the term "absorbent core" 30 refers to the component of the absorbent article 10 having the most absorbent capacity and that comprises an absorbent material. Referring to FIGS. 9-11, in some instances, a core absorbent material 72 may be positioned within a core bag or a core wrap or cover 74 made from, for example, a nonwoven web. The core absorbent material 72 may be profiled or not profiled, depending on the specific absorbent article. The absorbent core 30 may comprise, consist essentially of, or consist of, a core wrap 74, core absorbent material 72, and core glue or adhesive enclosed within the core wrap 74. The core wrap 74 may be constructed with one or more nonwoven webs. These nonwoven webs may comprise non-phthalate catalyst polymers. The nonwoven webs may also comprise bio-based materials, including plant-based fibers and/or bio-based materials such as bio-based polyolefins.

The core absorbent material 72 may comprise superabsorbent polymers, a mixture of superabsorbent polymers and air felt (also referred to herein as absorbent pulp), and/or only air felt. The core absorbent material may comprise just the core absorbent materials alone and not include the core wrap, core wrap nonwovens, core glues or adhesives enclosed within the core wrap. The core glue or adhesive may be used to immobilize the superabsorbent polymer particles within the core wrap 74. In some instances, the core absorbent material 72 may comprise at least 50%, at least 60%, at least 70%, at least 80%, at least 85%, at least 90%, at least 95%, at least 99%, or up to 100% superabsorbent polymers, by weight of the core absorbent material 72. In some instances, the core absorbent material 72 may be free of air felt, or at least mostly free of air felt. The absorbent core periphery, which may be the periphery of the core wrap 74, may define any suitable shape, such as rectangular "T," "Y," "hour-glass," or "dog-bone" shaped, for example. An absorbent core periphery having a generally "dog bone" or "hour-glass" shape may taper along its width towards the crotch region 14 of the absorbent article 10.

Referring to FIGS. 9-11, the absorbent core 30 may have areas having little or no core absorbent material 72, where a wearer-facing surface of the core wrap 74 may be joined to a garment-facing surface of the core wrap 74. These areas having little or no core absorbent material 72 may be referred to as "channels" 76. These channels 76 can embody any suitable shapes and any suitable number of channels 76 may be provided. In other instances, the absorbent core 30 may be embossed to create the impression of channels. The absorbent core 30 in FIGS. 9-11 is merely an example absorbent core. Many other absorbent cores with or without channels are also within the scope of the present disclosure.

The superabsorbent polymers of the core absorbent material 72 may comprise a bio-based acrylic acid. In some examples, the superabsorbent polymers may have a bio-based content of from about 5% to about 100%, from about 10% to about 100%, from about 25% to about 100%, from about 40% to about 100%, from about 50% to about 100%, from about 75% to about 100%, or from about 90% to about 100% and all ranges subsumed therein. Superabsorbent polymers comprising a desired bio-based content may be obtained, for example, by mixing acrylic acid derived from conventional (i.e., petroleum-based) sources with bio-based acrylic acid and forming the superabsorbent polymers with the acrylic acid mixture. Superabsorbent polymers comprising the desired bio-based content may also be obtained, for example, by mixing superabsorbent polymers made from conventional acrylic acid with superabsorbent polymers made from bio-based acrylic acid.

Bio-based acrylic acid may be produced using one or more bio-based intermediates. For example, production of conventional, petroleum-based acrylic acid may involve use of petroleum naphtha derived from refining of crude oil to produce propane and/or propene, which may then be oxidized to produce acrylic acid. Bio-based naphtha, which may be derived from renewable materials such plant oils (e.g., palm oil, tall oil, etc.) and animal fat, including waste oils and fats, may be used to produce propane that is then oxidized to produce bio-based acrylic acid. Bio-based propane may be produced from similar renewable sources such as plant and animal waste products and may also occur as a waste product from biofuel production. This bio-based propane may then be oxidized to produce bio-based acrylic acid. In addition, bio-based acrylic acid may be produced (directly) by dehydration of bio-based lactic acid or 3-hydroxy propionic acid, which may be derived from, for example, microbial fermentation of plant-based sources (e.g., corn, rice, waste paper, etc.) and from waste products such as glycerol obtained from biofuel production. These methods may produce acrylic acid of high purity, i.e., a purity of about 98 weight % acrylic acid or higher. While not wishing to be bound by theory, higher purity acrylic acid is critical for achieving high performance superabsorbent polymer characteristics, as well as consumer acceptable performance by the absorbent article. Bio-based acrylic acid and methods of production are further described in U.S. Pat. Appl. Pub. No. 2007/0219521 and U.S. Pat. Nos. 8,703,450; 9,630,901; and 9,822,197.

Barrier Leg Cuffs/Leg Elastics

Referring to FIGS. 1 and 2, for example, the absorbent article 10 may comprise one or more pairs of barrier leg cuffs 32 and one or more pairs of outer leg elastics 34. The barrier leg cuffs 32 may be positioned laterally inboard of leg elastics 34. Each barrier leg cuff 32 may be formed by a piece of nonwoven web as described herein that is bonded via a chassis glue or adhesive and/or one or more non-adhesive methods as described herein to the absorbent article 10 so that the barrier leg cuff 32 extends upwards from a wearer-facing surface 4 of the absorbent article 10 and provides improved containment of body exudates approximately at the junction of the torso and legs of the wearer. Useful materials may include, but are not limited to, spunbond-meltblown-spunbond (SMS) nonwoven webs. Such webs may comprise non-phthalate catalyst polypropylene fibers and/or plant-based fibers. Furthermore, these nonwoven webs may also comprise bio-based materials, including plant-based fibers and/or bio-based materials such as bio-based polyolefins.

The barrier leg cuffs 32 are delimited by a proximal edge joined directly or indirectly to the topsheet 26 and/or the backsheet 28 and a free terminal edge, which is intended to contact and form a seal with the wearer's skin. The barrier leg cuffs 32 may extend at least partially between the front end edge 18 and the back end edge 20 of the absorbent article 10 on opposite sides of the central longitudinal axis 50 and may be at least present in the crotch region 14. The barrier leg cuffs 32 may each comprise one or more elastics 33 (e.g., elastic strands or strips) near or at the free terminal edge. These elastics 33 cause the barrier leg cuffs 32 to help form a seal around the legs and torso of a wearer. The outer leg elastics 34 extend at least partially between the front end edge 18 and the back end edge 20 of the absorbent article 10. The leg elastics 34 essentially cause portions of the absorbent article 10 proximate to the chassis side edges 22, 24 to help form a seal around the legs of the wearer. The leg elastics 34 may extend at least within the crotch region 14. The leg elastics may be latex-free.

Elastic Waistband

Referring to FIGS. 1 and 2, the absorbent article 10 may comprise one or more elastic waistbands 36. The elastic waistbands 36 may be positioned on the garment-facing surface 2 or the wearer-facing surface 4. As an example, a first elastic waistband 36 may be present in the front waist region 12 near the front belt end edge 18 and a second elastic waistband 36 may be present in the back waist region 16 near the back end edge 20. The elastic waistbands 36 may comprise one or two layers of nonwoven webs with an elastic film or elastic strands therebetween. The elastic waistbands 36 may aid in sealing the absorbent article 10 around a waist of a wearer and at least inhibiting bodily exudates from escaping the absorbent article 10 through the waist opening circumference. In some instances, an elastic waistband may fully surround the waist opening circumference of an absorbent article.

Acquisition/Distribution Materials

Referring to FIGS. 1, 2, 7, and 8, one or more acquisition and/or distribution materials 38 (also referred to herein as "acquisition material(s)") may be present at least partially intermediate the topsheet 26 and the absorbent core 30. The acquisition materials 38 are typically hydrophilic materials that provide significant wicking of bodily exudates. These materials may dewater the topsheet 26 and quickly move bodily exudates into the absorbent core 30. The acquisition materials 38 may comprise one or more nonwoven materials, foams, cellulosic materials, cross-linked cellulosic materials, air laid cellulosic nonwoven materials, spunlace materials, or combinations thereof, for example. The cellulosic materials and cross-linked cellulosic materials may be bleached, but preferably not via chlorine-bleaching so as to be total chlorine free. Hydrogen peroxide is one exemplary bleaching material that is useful in making acquisition materials 38 that are totally chlorine-free. In other embodiments, acquisition and/or distribution materials may comprise non-phthalate catalyst polypropylene fibers and/or plant-based fibers. Furthermore, these nonwoven webs may also comprise bio-based materials, including plant-based fibers and/or bio-based materials such as bio-based polyethylene, bio-based polypropylene, other bio-based polyolefins, bio-based polyesters, and combinations thereof including bi-component fiber configurations.

In some instances, portions of the acquisition materials 38 may extend through portions of the topsheet 26, portions of the topsheet 26 may extend through portions of the acquisition materials 38, and/or the topsheet 26 may be nested with the acquisition materials 38. Typically, an acquisition material 38 may have a width and length that are smaller than the width and length of the topsheet 26. The acquisition material 38 may be a secondary topsheet in the feminine pad context. The acquisition material 38 may have one or more channels as described above with reference to the absorbent core 30 (including the embossed version). The channels in the acquisition material 38 may align or not align with channels 76 in the absorbent core 30. In an example, a first acquisition material may comprise a nonwoven material and as second acquisition material may comprise a cross-linked cellulosic material.

Landing Zone

Referring to FIGS. 1 and 2, the absorbent article 10 may have a landing zone area 44 that is formed in a portion of the garment-facing surface 2 of the outer cover material 40. The landing zone area 44 may be in the back waist region 16 if the absorbent article 10 fastens from front to back or may be in the front waist region 12 if the absorbent article 10 fastens back to front. In some instances, the landing zone 44 may be or may comprise one or more discrete nonwoven materials that are attached to a portion of the outer cover material 40 in the front waist region 12 or the back waist region 16 depending upon whether the absorbent article 10 fastens in the front or the back. In essence, the landing zone 44 is configured to receive the fasteners 46 and may comprise, for example, a plurality of loops configured to be engaged with, a plurality of hooks on the fasteners 46, or vice versa. Landing zone materials, landing zone nonwovens, landing zone nonwovens comprising loops, and fastener hooks may contain polymers containing bio-based content.

Wetness Indicator/Graphics

Referring to FIG. 1, the absorbent articles 10 of the present disclosure may comprise graphics 78 and/or wetness indicators 80 that are visible from the garment-facing surface 2. The graphics 78 may be printed on the landing zone 40, the backsheet 28, and/or at other locations. The wetness indicators 80 are typically applied to the absorbent core facing side of the backsheet 28, so that they can be contacted by bodily exudates within the absorbent core 30. In some instances, the wetness indicators 80 may form portions of the graphics 78. For example, a wetness indicator may appear or disappear and create/remove a character within some graphics. In other instances, the wetness indicators 80 may coordinate (e.g., same design, same pattern, same color) or not coordinate with the graphics 78.

In one form, the wetness indicator 80 may comprise a color changing composition based upon a pH change when contacted with a chemical compound typically contained in urine. The color changing composition may be devoid of poly-aromatic hydrocarbons.

Front and Back Ears

Referring to FIGS. 1 and 2, as referenced above, the absorbent article 10 may have front and/or back ears 47, 42 in a taped diaper context. Only one set of ears may be required in most taped diapers. The single set of ears, e.g., the back ears 42, may comprise tape tabs 43 comprising fasteners 46 (also referred to herein as ear hooks) configured to engage the landing zone or landing zone area 44. If two sets of ears are provided, in most instances, only one set of the ears may have fasteners 46, with the other set being free of fasteners. The ears, or portions thereof, may be elastic or may have elastic panels. In an example, a stretch or elastic film or stretch or elastic strands may be positioned intermediate a first nonwoven web and a second nonwoven web. In one embodiment, the back set of ears 42 are made from first and second nonwoven webs with an elastic film or elastic strands therebetween, while the front set of ears 47 are made from a generally non-elastic nonwoven web. The nonwoven materials may comprise non-phthalate catalyst polypropylene fibers. Furthermore, these nonwoven materials or webs may also comprise bio-based materials, including plant-based fibers and/or bio-based materials such as bio-based polyolefins.

The elastic film may or may not be apertured. The ears 42, 47 may be shaped. The ears 42, 47 may be integral (e.g., extension of the outer cover material 40, the backsheet 28, and/or the topsheet 26) or may be discrete components attached to a chassis 52 of the absorbent article 10 on a wearer-facing surface 4, on the garment-facing surface 2, or intermediate the two surfaces 4, 2.

Adhesives

Adhesives as described herein may be employed to affix one component to another component in the absorbent article's final assembly. Adhesives may also be employed to immobilize sub-components, such as, for example, particulate matter within an absorbent core component. The adhesives in some instances may be devoid of added fluorescence. Furthermore, adhesive may also comprise bio-based materials, including bio-based materials such as bio-based polyolefins, bio-based polyethylenes, bio-based polypropylenes, bio-based alpha olefin polyolefins, and combinations thereof.

Sensors

Referring again to FIG. 1, the absorbent articles of the present disclosure may comprise a sensor system 82 for monitoring changes within the absorbent article 10. The sensor system 82 may be discrete from or integral with the absorbent article 10. The absorbent article 10 may comprise sensors that can sense various aspects of the absorbent article 10 associated with insults of bodily exudates such as urine and/or BM (e.g., the sensor system 82 may sense variations in temperature, humidity, presence of ammonia or urea, various vapor components of the exudates (urine and feces), changes in moisture vapor transmission through the absorbent articles garment-facing layer, changes in translucence of the garment-facing layer, and/or color changes through the garment-facing layer). Additionally, the sensor system 82 may sense components of urine, such as ammonia or urea and/or byproducts resulting from reactions of these components with the absorbent article 10. The sensor system 82 may sense byproducts that are produced when urine mixes with other components of the absorbent article 10 (e.g., adhesives, agm). The components or byproducts being sensed may be present as vapors that may pass through the garment-facing layer. It may also be desirable to place reactants in the absorbent article that change state (e.g. color, temperature) or create a measurable byproduct when mixed with urine or BM. The sensor system 82 may also sense changes in pH, pressure, odor, the presence of gas, blood, a chemical marker or a biological marker or combinations thereof. The sensor system 82 may have a component on or proximate to the absorbent article that transmits a signal to a receiver more distal from the absorbent article, such as an iPhone, for example. The receiver may output a result to communicate to the caregiver a condition of the absorbent article 10. In other instances, a receiver may not be provided, but instead the condition of the absorbent article 10 may be visually or audibly apparent from the sensor on the absorbent article.

Packages

The absorbent articles of the present disclosure may be placed into packages. The packages may comprise a polymeric bag and an optional carton surrounding at least a portion of the polymeric bag. The polymeric bag may comprise bio-based polyolefin in some forms. The optional carton may be made of fiberboard and may contain recycled material or a blend of recycled and virgin material. Each package may comprise a plurality of absorbent articles.

Communication in the form of graphics and/or indicia relating to properties of the absorbent articles may be formed on, printed on, positioned on, and/or placed on outer portions of the packages. For example, the communication may relate to the absence of certain undesirable materials, such as chlorine, perfume, scent, fragrance, lotion, non-phthalate-catalyst polypropylene, adhesives having added florescence, and green number 7 dye. The communication may also relate to features of the contained absorbent articles, such as, that the absorbent articles have cotton (via cotton seal icon) or plant-based materials.

The absorbent articles may be packed under compression so as to reduce the size of the packages, while still providing an adequate amount of absorbent articles per package. By packaging the absorbent articles under compression, caregivers can easily handle and store the packages, while also providing distribution savings to manufacturers owing to the size of the packages.

Accordingly, packages of the absorbent articles of the present disclosure may have an In-Bag Stack Height of less than about 110 mm, less than about 105 mm, less than about 100 mm, less than about 95 mm, less than about 90 mm, less than about 85 mm, less than about 80 mm, less than about 78 mm, less than about 76 mm, less than about 74 mm, less than about 72 mm, or less than about 70 mm, specifically reciting all 0.1 mm increments within the specified ranges and all ranges formed therein or thereby, according to the In-Bag Stack Height Test described herein. Alternatively, packages of the absorbent articles of the present disclosure may have an In-Bag Stack Height of from about 70 mm to about 110 mm, from about 70 mm to about 105 mm, from about 70 mm to about 100 mm, from about 70 mm to about 95 mm, from about 70 mm to about 90 mm, from about 70 mm to about 85 mm, from about 72 mm to about 80 mm, or from about 74 mm to about 78 mm, specifically reciting all 0.1 mm increments within the specified ranges and all ranges formed therein or thereby, according to the In-Bag Stack Height Test described herein.

Figure 16:
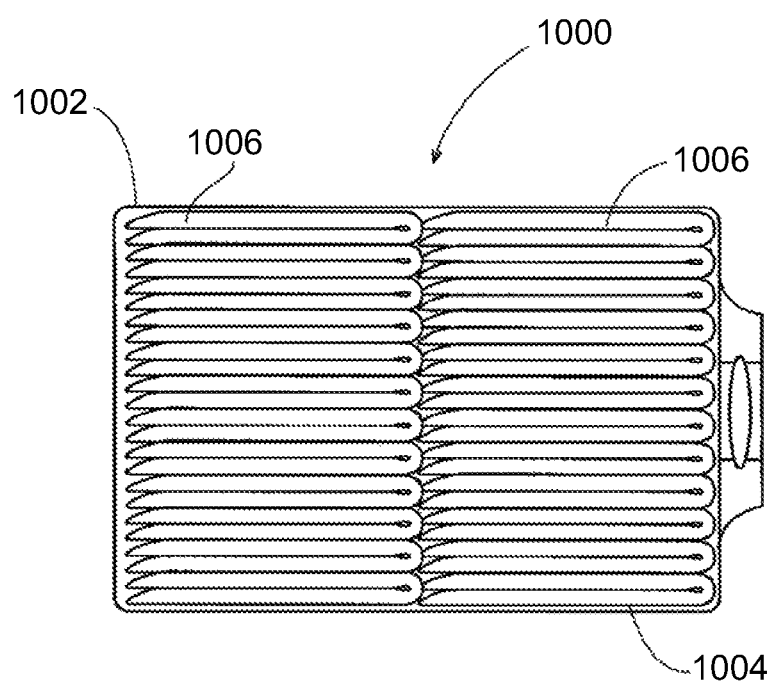
FIG. 16 is a side view of a package containing a plurality of absorbent articles.

FIG. 16 illustrates an example package 1000 comprising a plurality of absorbent articles 1004. The package 1000 defines an interior space 1002 in which the plurality of absorbent articles 1004 are situated. The plurality of absorbent articles 1004 are arranged in one or more stacks 1006.

Arrays

"Array" means a display of packages comprising disposable absorbent articles of different article constructions (e.g., different elastomeric materials [compositionally and/or structurally] in the side panels, side flaps and/or belts flaps, different graphic elements, different product structures, fasteners or lack thereof). The packages may have the same brand and/or sub-brand and/or the same trademark registration and/or having been manufactured by or for a common manufacturer and the packages may be available at a common point of sale (e.g. oriented in proximity to each other in a given area of a retail store). An array is marketed as a line-up of products normally having like packaging elements (e.g., packaging material type, film, paper, dominant color, design theme, etc.) that convey to consumers that the different individual packages are part of a larger line-up. Arrays often have the same brand, for example, "Huggies," and same sub-brand, for example, "Pull-Ups." A different product in the array may have the same brand "Huggies" and the sub-brand "Little Movers." The differences between the "Pull-Ups" product of the array and the "Little Movers" product in the array may include product form, application style, different fastening designs or other structural elements intended to address the differences in physiological or psychological development. Furthermore, the packaging is distinctly different in that "Pull-Ups" is packaged in a predominately blue or pink film bag and "Little Movers" is packaged in a predominately red film bag.

Further regarding "Arrays," as another example an array may be formed by different products having different product forms manufactured by the same manufacturer, for example, "Kimberly-Clark", and bearing a common trademark registration for example, one product may have the brand name "Huggies," and sub-brand, for example, "Pull-Ups." A different product in the array may have a brand/sub-brand "Good Nites" and both are registered trademarks of The Kimberly-Clark Corporation and/or are manufactured by Kimberly-Clark. Arrays also often have the same trademarks, including trademarks of the brand, sub-brand, and/or features and/or benefits across the line-up. "On-line Array" means an "Array" distributed by a common on-line source.

Sanitary Napkin

Figure 12:
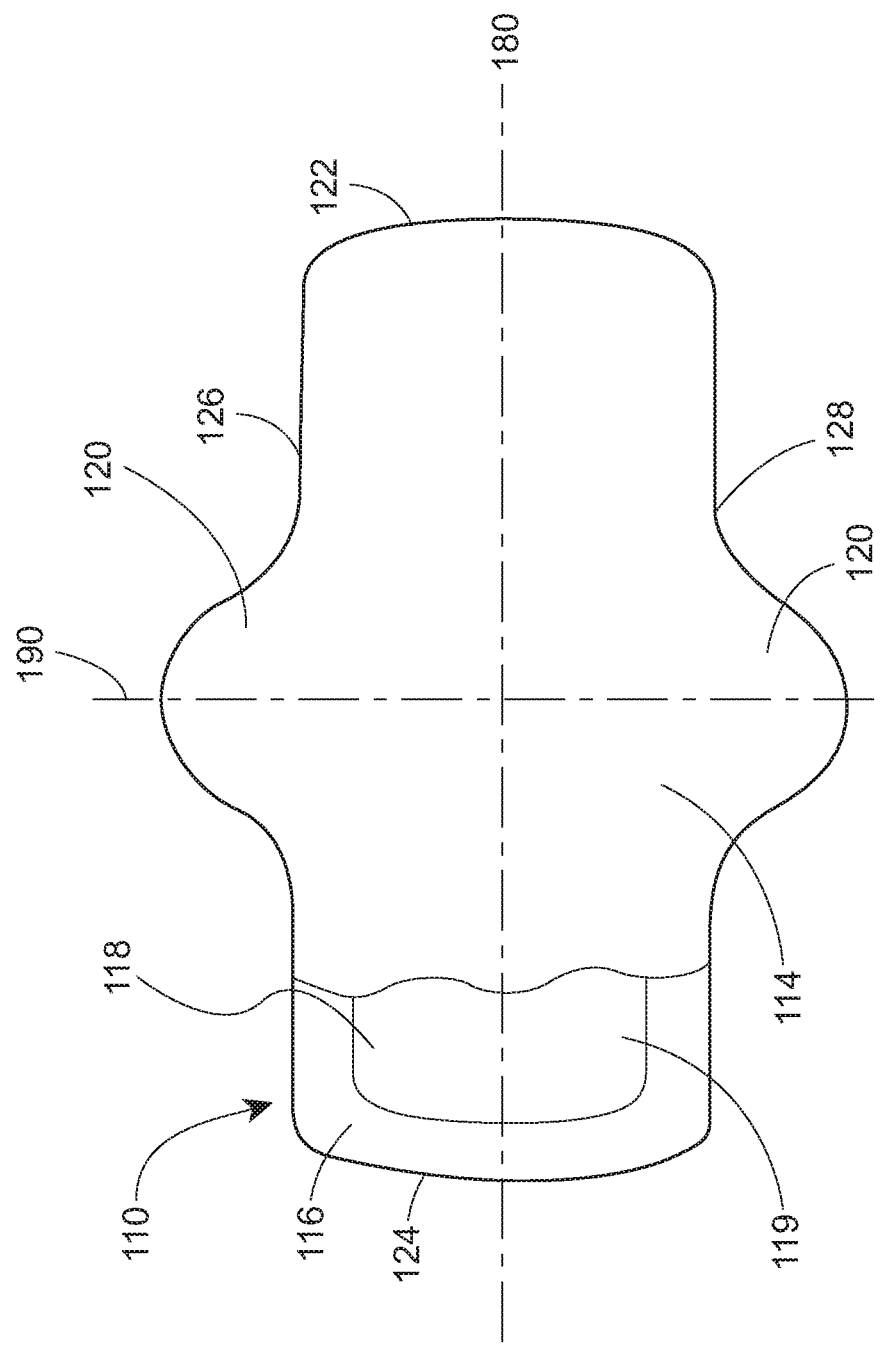
FIG. 12 is a plan view of an example absorbent article of the present disclosure that is a sanitary napkin.

Referring to FIG. 12, an absorbent article of the present disclosure may be a sanitary napkin 110. The sanitary napkin 110 may comprise a liquid permeable topsheet 114, a liquid impermeable, or substantially liquid impermeable, backsheet 116, and an absorbent core 118. The liquid impermeable backsheet 116 may or may not be vapor permeable. The absorbent core 118 may have any or all of the features described herein with respect to the absorbent core 30 and, in some forms, may have a secondary topsheet 119 (STS) instead of the acquisition materials 38 disclosed above. The STS 119 may comprise one or more channels, as described above (including the embossed version). In some forms, channels in the STS 119 may be aligned with channels in the absorbent core 118. The sanitary napkin 110 may also comprise wings 120 extending outwardly with respect to a longitudinal axis 180 of the sanitary napkin 110. The sanitary napkin 110 may also comprise a lateral axis 190. The wings 120 may be joined to the topsheet 114, the backsheet 116, and/or the absorbent core 118. The sanitary napkin 110 may also comprise a front edge 122, a back edge 124 longitudinally opposing the front edge 122, a first side edge 126, and a second side edge 128 longitudinally opposing the first side edge 126. The longitudinal axis 180 may extend from a midpoint of the front edge 122 to a midpoint of the back edge 124. The lateral axis 190 may extend from a midpoint of the first side edge 128 to a midpoint of the second side edge 128. The sanitary napkin 110 may also be provided with additional features commonly found in sanitary napkins as is known in the art.

Example Cross-Sections of Absorbent Articles

Figure 13:
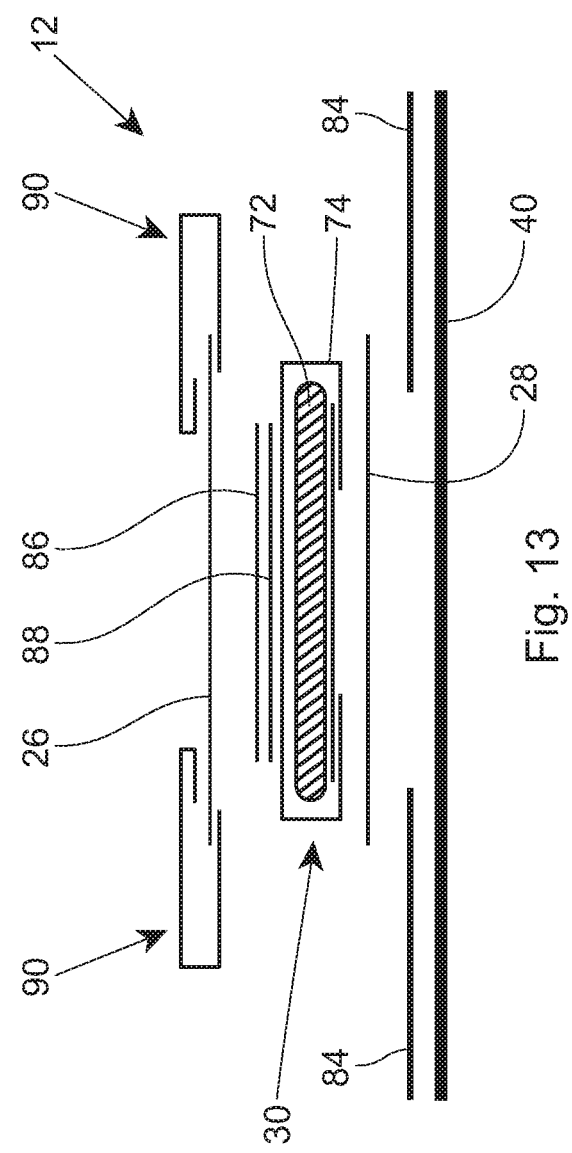
FIG. 13 is an example cross-sectional view taken within a front waist region of an absorbent article.
Figure 14:
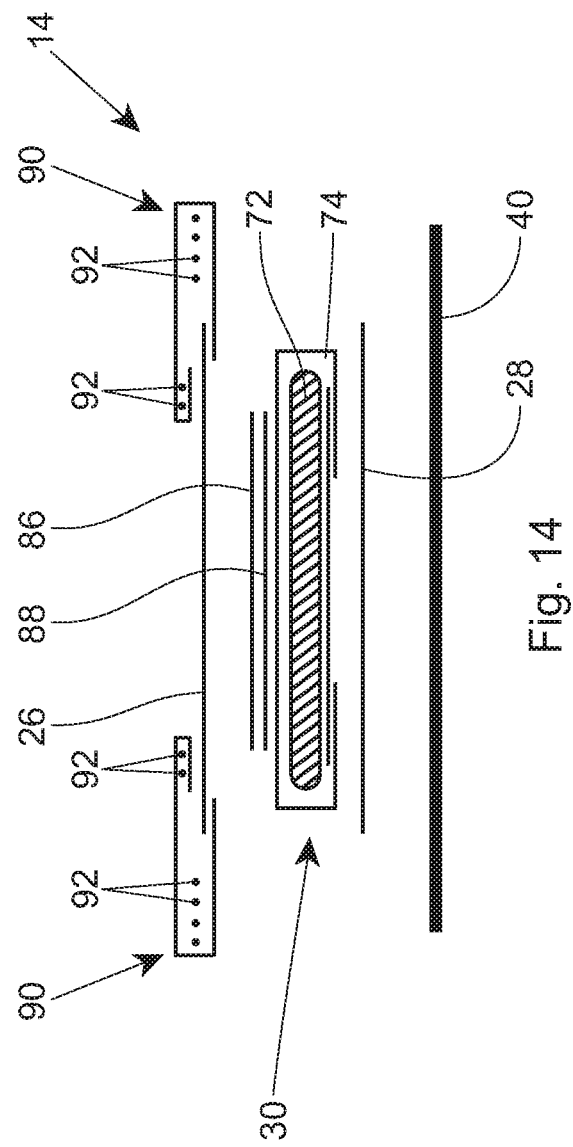
FIG. 14 is an example cross-sectional view taken within a crotch region of an absorbent article.
Figure 15:
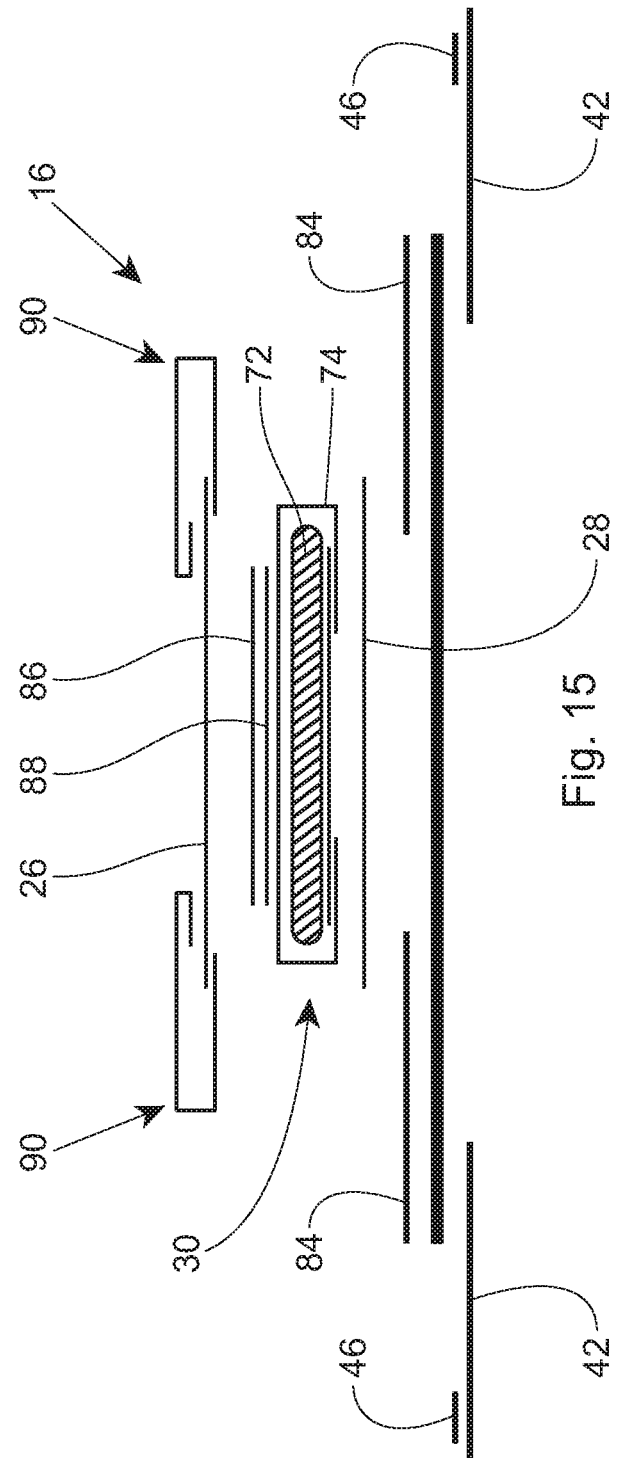
FIG. 15 is an example cross-sectional view taken within a back waist region of an absorbent article.

FIGS. 13-15 illustrate example cross-sectional views of absorbent articles within the scope of the present disclosure. FIG. 13 is an example cross-sectional view taken within a front waist region 12 of an absorbent article. FIG. 14 is an example cross-sectional view taken within a crotch region 14 of an absorbent article. FIG. 15 is an example cross-sectional view taken within a back waist region 16 of an absorbent article. In FIGS. 13-15, an outer cover material is element 40, a liquid permeable topsheet is element 26, opacity patches are elements 84, a liquid impermeable backsheet is element 28, an absorbent core is element 30, with the core wrap being element 74, an absorbent material is element 72, and a distribution material is element 86. The distribution material 86 may comprise cross-linked cellulosic material and may be optional. An acquisition material is element 88. Barrier leg cuffs are elements 90. Elastics in the barrier leg cuffs are elements 92. Back ears are elements 42. Fasteners on the back ears 42 are elements 46. Construction glues and/or bonds between the various layers and/or components have been removed for clarity. Other cross-sectional configurations known to those of skill in the art are also within the scope of the present disclosure.

Absorbent Articles Comprising Recyclable and Sustainable Materials

The example absorbent articles of the present disclosure as shown in FIGS. 1-16 may comprise one or more recyclable materials and one or more components comprising a bio-based material. In one example, an absorbent article according to the present disclosure may comprise a topsheet 26, 114; a backsheet 28, 116 joined to the topsheet; and an absorbent core 30, 118 positioned intermediate the topsheet and the backsheet and comprising a core absorbent material. The core absorbent material may comprise superabsorbent polymers with a bio-based content from about 5% to about 100%, as determined using ASTM D6866-10, method B, and the absorbent article may comprise a polyolefin content of at least about 90% by weight, based on a total weight of the absorbent article excluding the core absorbent material. In some particular examples, the polyolefin content of the absorbent article may comprise at least about 95% by weight, at least about 97% by weight, at least about 98% by weight, or at least about 99% by weight, based on a total weight of the absorbent article excluding the core absorbent material.

In another example, an absorbent article according to the present disclosure, which may be disposable, may comprise the following 17 enumerated components: (1) a topsheet 26, 114; (2) a backsheet film 28, 116; (3) a backsheet nonwoven web (e.g., an outer cover material 40); (4) a landing zone 44; (5) a stretch or elastic ear film; (6) a back ear nonwoven web; (7) tape tabs 43; (8) ear hooks 46; (9) a front ear nonwoven web; (10) a waist feature nonwoven web; (11) waist feature elastics, such an elastic film or elastic strands; (12) a barrier leg cuff nonwoven web; (13) outer leg elastics 34; (14) an acquisition material 38; (15) a core cover nonwoven web; (16) chassis adhesives; and (17) core adhesives, in which the topsheet is joined to a backsheet 28, 116 defined by the backsheet film and the backsheet nonwoven web and the core cover nonwoven web and a core absorbent material 72 are positioned intermediate the topsheet and the backsheet. At least 13 of the 17 enumerated components of the absorbent article comprise one or more polyolefins, and the core absorbent material comprises superabsorbent polymers with a bio-based content from about 5% to about 100%, as determined using ASTM D6866-10, method B. In some particular examples, at least 14 or at least 15 or at least 16 of the 17 enumerated components of the absorbent article may comprise one or more polyolefins. In other particular examples, at least one, at least two, at least three, at least four, or at least five of the 17 enumerated components that comprise one or more polyolefins may comprise a bio-based polyolefin with a bio-based content from about 5% to about 100% using ASTM D6866-10, method B. In further particular examples, as described herein, at least one of the 17 enumerated components that comprises one or more polyolefins may comprise a bio-based polyolefin with a bio-based content from about 10% to about 100%, from about 25% to about 100%, from about 40% to about 100%, from about 50% to about 100%, from about 75% to about 100%, or from about 90% to about 100%, as determined using ASTM D6866-10, method B.

In a further example, an absorbent article according to the present disclosure, which may be disposable and may be in the form of a pant as described herein, may comprise the following 11 enumerated components: (1) a topsheet; (2) a backsheet film; (3) a backsheet nonwoven web; (4) belt elastics; (5) a belt nonwoven web; (6) chassis adhesives; (7) a barrier leg cuff nonwoven web; (8) outer leg elastics; (9) an acquisition material; (10) a core cover nonwoven web; and (11) core adhesives; in which the topsheet is joined to a backsheet 28, 116 defined by the backsheet film and the backsheet nonwoven web and the core cover nonwoven web and the core absorbent material are positioned intermediate the topsheet and the backsheet. At least 7 of the 11 enumerated components of the absorbent article comprise one or more polyolefins, and the core absorbent material comprises superabsorbent polymers with a bio-based content from about 5% to about 100%, as determined using ASTM D6866-10, method B. In some particular examples, at least 8 or at least 9 or at least 10 of the 11 enumerated components of the absorbent article may comprise one or more polyolefins. In other particular examples, at least one, at least two, at least three, at least four, or at least five of the 11 enumerated components that comprise one or more polyolefins may comprise a bio-based polyolefin with a bio-based content from about 5% to about 100% using ASTM D6866-10, method B. In further particular examples, as described herein, at least one of the 11 enumerated components that comprises one or more polyolefins may comprise a bio-based polyolefin with a bio-based content from about 10% to about 100%, from about 25% to about 100%, from about 40% to about 100%, from about 50% to about 100%, from about 75% to about 100%, or from about 90% to about 100%, as determined using ASTM D6866-10, method B.

In all absorbent articles according to the present disclosure, the bio-based content of the superabsorbent polymers may comprise from about 10% to about 100%, from about 25% to about 100%, from about 40% to about 100%, from about 50% to about 100%, from about 75% to about 100%, or from about 90% to about 100%, and all ranges subsumed therein, as determined using ASTM D6866-10, method B as described herein. In some particular examples, the superabsorbent polymers of the core absorbent material may comprise a bio-based acrylic acid or may be polymerized from bio-based acrylic acid, as described herein.

In all absorbent articles according to the present disclosure, the core absorbent material may comprise, based on the total weight of the core absorbent material, at least about 60% by weight or at least about 70% by weight or at least about 90% by weight of the superabsorbent polymers. In some particular instances, the core absorbent material may further comprise an absorbent pulp. In other particular instances, the core absorbent material may be substantially free of the absorbent pulp. In all absorbent articles according to the present disclosure, a package comprising a plurality of the absorbent articles may have an In-Bag Stack Height of from about 70 mm to about 110 mm, according to the In-Bag Stack Height Test described herein.

One or more of the components of the example absorbent articles according to the present disclosure may be formed from one or more polyolefins such that the absorbent articles comprise a polyolefin content of at least about 90% by weight, based on a total weight of the absorbent article excluding the core absorbent material, as described herein. In some aspects, absorbent articles according to the present disclosure may comprise a polyolefin content of at least about 95% by weight, at least about 97% by weight, at least 98% by weight, or at least about 99% by weight, based on a total weight of the absorbent article excluding the core absorbent material.

In some examples, polyolefins may include ethylene polymers (e.g., low density polyethylene ("LDPE"), high density polyethylene ("HDPE"), linear low density polyethylene ("LLDPE"), etc., propylene homopolymers (e.g., syndiotactic, atactic, isotactic, etc.), ethylene copolymers, propylene copolymers, a blend or blends thereof, and so forth. In one particular example, the polymer may be a propylene polymer, such as homo polypropylene or a copolymer of propylene. The propylene polymer may, for instance, be formed from a substantially isotactic polypropylene homopolymer or a copolymer containing equal to or less than about 10 wt. % of other monomers, i.e., at least about 90% by weight propylene. Such homopolymers may have a melting point of from about 140° C. to about 170° C. The melting temperature may be determined using differential scanning calorimetry ("DSC") in accordance with ASTM D-3417.

In other examples, the polyolefin may be a copolymer of ethylene or propylene with another alpha-olefin, such as a C3-C20 alpha-olefin or C3-C12 alpha-olefin. Specific examples of suitable alpha-olefins may include 1-butene; 3-methyl-1-butene; 3,3-dimethyl-1-butene; 1-pentene; 1-pentene with one or more methyl, ethyl, or propyl substituents; 1-hexene with one or more methyl, ethyl, or propyl substituents; 1-heptene with one or more methyl, ethyl, or propyl substituents; 1-octene with one or more methyl, ethyl, or propyl substituents; 1-nonene with one or more methyl, ethyl, or propyl substituents; ethyl, methyl, or dimethyl-substituted 1-decene; 1-dodecene; and styrene. Particularly desired alpha-olefin comonomers are 1-butene, 1-hexene, and 1-octene. The ethylene or propylene content of such copolymers may be from about 60 mole % to about 99 mole %, in some examples from about 80 mole % to about 98.5 mole %, and in some examples, from about 87 mole % to about 97.5 mole %. The alpha-olefin content may likewise range from about 1 mole % to about 40 mole %, in some examples from about 1.5 mole % to about 15 mole %, and in some examples, from about 2.5 mole % to about 13 mole %.

Exemplary olefin copolymers for use in absorbent articles according to the present disclosure may include ethylene-based copolymers available under the designation EXACT™ (ExxonMobil Chemical Company). Other suitable ethylene copolymers are available under the designation ENGAGE™, AFFINITY™, DOWLEX™ (LLDPE), and ATTANE™ (ULDPE) (Dow Chemical Company). Other suitable ethylene polymers are described in U.S. Pat. Nos. 4,937,299; 5,218,071; 5,272,236; and 5,278,272. Suitable propylene copolymers are also commercially available under the designations VISTAMAXX® (ExxonMobil); FINA™ (e.g., 8573; Atofina Chemicals); TAFMER™ (Mitsui Petrochemical Industries); and VERSIFY™ (Dow). Suitable polypropylene homopolymers may include PP3155™ and ACHIEVE™ resins (ExxonMobil); and Polypropylene M3661™ resin (Total Petrochemicals & Refining USA, Inc.). Other examples of suitable propylene polymers are described in U.S. Pat. Nos. 6,500,563; 5,539,056; and 5,596,052.

Any of a variety of known techniques may generally be employed to form the olefin copolymers. For instance, olefin polymers may be formed using a free radical or a coordination catalyst (e.g., Ziegler-Natta). The olefin polymer may be formed from a single-site coordination catalyst, such as a metallocene catalyst. Such a catalyst system produces ethylene copolymers in which the comonomer is randomly distributed within a molecular chain and uniformly distributed across the different molecular weight fractions. Metallocene-catalyzed polyolefins are described, for instance, in U.S. Pat. Nos. 5,571,619; 5,322,728; 5,472,775; 5,272,236; and 6,090,325. Examples of metallocene catalysts include bis(n-butylcyclopentadienyl)titanium dichloride, bis(n-butylcyclopentadienyl)zirconium dichloride, bis(cyclopentadienyl)scandium chloride, bis(indenyl)zirconium dichloride, bis(methylcyclopentadienyl)titanium dichloride, bis(methylcyclopentadienyl)zirconium dichloride, cobaltocene, cyclopentadienyltitanium trichloride, ferrocene, hafnocene dichloride, isopropyl(cyclopentadienyl,-1-flourenyl)zirconium dichloride, molybdocene dichloride, nickelocene, niobocene dichloride, ruthenocene, titanocene dichloride, zirconocene chloride hydride, zirconocene dichloride, and so forth. Polymers made using metallocene catalysts typically have a narrow molecular weight range. For instance, metallocene-catalyzed polymers may have polydispersity numbers (Mw/Mn) of below 4, controlled short chain branching distribution, and controlled isotacticity. Polyolefins are further discussed in U.S. Pat. Appl. Pub. Nos. 2016/0101208; 2016/0114071; 2016/0115291; 2016/0122484; and 2016/0130731.

In some instances, one or more of the components of the absorbent articles according to the present disclosure may comprise a nonwoven web or material comprising one or more thermoplastic fibers formed from one or more fiber-forming polyolefins. As used herein, the terms "nonwoven material" or "nonwoven web" may refer to a material or web having a structure of individual fibers or threads that are interlaid, but not in a repeating pattern as in a woven or knitted fabric, which latter types of fabric typically do not have randomly oriented or substantially randomly oriented fibers. Nonwoven materials will have a machine direction (MD) and a cross direction (CD) as is commonly known in the art of web manufacture. By "substantially randomly oriented" is meant that, due to processing conditions of a precursor web, there may be a higher amount of fibers oriented in the MD than the CD, or vice versa. For example, in spunbonding and meltblowing processes continuous strands of fibers are deposited on a support moving in the MD. Despite attempts to make the orientation of the fibers of the spunbond or meltblown nonwoven web truly "random", usually a slightly higher percentage of fibers are oriented in the MD as opposed to the CD.

The fibers may comprise unbonded fibers, entangled fibers, tow fibers, or the like. The fibers may be extensible and/or elastic, and may be pre-stretched for processing. The fibers of the nonwoven material may be formed using many known processes, such as, for example, air laying processes, wetlaid processes, meltblowing processes, spunbonding processes, and carding processes. The fibers in the nonwoven material may then be bonded via spunlacing processes, hydroentangling, calendar bonding, through-air bonding and resin bonding. Some of the nonwoven materials formed using these processes may have bond sites where the fibers are bonded together.

In other instances, one or more of the components of the absorbent articles according to the present disclosure may comprise a polymeric film comprising one or more thermoplastic materials such as polyolefins. Thermoplastic materials have properties that depend on their composition and temperature. For example, a thermoplastic polymer exhibits viscoelasticity when above its glass transition temperature (but below the melt temperature range) and may be extruded or cast as substantially planar films. In addition, in this temperature range, thermoplastic polymeric films may be formed as, or altered to, a non-planar configuration. In some particular examples, the polymeric film may be deformable. As used herein, the term "deformable" may describe a material that, when stretched beyond its elastic limit, will substantially retain its newly formed conformation. Such deformable materials may be chemically homogeneous or heterogeneous, such as homopolymers and polymer blends, structurally homogeneous or heterogeneous, such as plain sheets or laminates, or any combination of such materials. In other particular examples, the polymeric film may be elastomeric.

In some aspects of the present disclosure, one or more of the components of the absorbent articles according to the present disclosure may comprise a single-layer film or a single-layer nonwoven material comprising one or more polyolefins. In other aspects, one or more of the components of the absorbent articles according to the present disclosure may comprise components that are a blend of fibers, a composite of two or more webs, a laminate of two or more webs, and/or other combination comprising one or more polyolefins. In some examples, one or more of the components of the absorbent articles may comprise a laminate with two or more layers of film, two more layers of nonwoven materials, or one or more layers each of a film and a nonwoven material joined together. The laminate may comprise, for example, a polymeric film that is bonded direct to a layer of nonwoven material. The polymeric film may also be extruded directly onto the nonwoven material.

In other aspects, the nonwoven material may comprise a mixture of two or more different fibers or a mixture of fibers and particles. Such mixtures may be formed by, for example, adding fibers and/or particulates to the gas stream in which the meltblown fibers or spunbond fibers are carried so that an intimate entangled co-mingling of fibers and other optional materials occurs prior to collection of the fibers.

In some aspects, at least one component of the absorbent articles according to the present disclosure may comprise one or more bio-based polyolefins. In some particular aspects, absorbent articles with at least one component comprising one or more bio-based polyolefins also comprise a core absorbent material with superabsorbent polymers comprising a bio-based acrylic acid, as described herein. Bio-based polyolefins may be obtained by polymerizing olefins derived from renewable resources to yield polyolefins having desired characteristics for use in one or more components of an absorbent article. The resulting bio-based polyolefins may be high density, medium density, low density, or linear-low density. These methods may produce polyolefins of high purity, i.e., a purity of about 98 weight % polyolefin or less than 2 weight % impurities associated with the bio-sourcing process. While not wishing to be bound by theory, higher purity polyolefin is critical for achieving high performance materials properties and minimal undesirable trace contaminants, as well as consumer acceptable performance by the absorbent article. Bio-based polyolefins are further discussed in U.S. Pat. Appl. Pub. Nos. 2011/0139657; 2011/0139658; 2011/0152812; and 2016/0206774 and U.S. Pat. No. 9,169,366.

The inventive combination of recycle friendly design, along with bio-based superabsorbent polymers, provides consumers and municipalities with the unexpected combined benefits of lowering the used absorbent article flow to the solid waste stream, creating a circular economy on a targeted high purity material, for example, polyolefins and superabsorbent polymers, and substitutes into absorbent articles superabsorbent polymers and polyolefins that are bio-based. While not wishing to be bound by theory, the inventive absorbent article designs described herein may make recycling of used absorbent articles a viable financial proposition because of the high purity waste streams possible from the recycling of the inventive absorbent articles, the lower capital cost for a recycling plant, and less complex and lower operating cost recycling operation. Further unexpectedly, the value of the higher purity waste streams may be further increased as they may be bio-based materials, which would potentially have more demand and command a higher price than similar petrolatum derived materials.

Exemplary bio-based polyolefins for use in the present invention include ethylene-based polymers available under the designations SHA7260™, SHE150™, SGM9450F™, SLL118™, SLL118/21™, SLL318™, SLH118™, SLH218™, SLH0820/30AF™, SBF0323HC™, SBF0323/12HC™, STN7006™, STS7006™, SEB853™, SEB853/72™, SPB681™, and SPB681/59™ (Braskem S.A.).

In some particular aspects, the bio-based content of a bio-based polyolefin for use in an absorbent article according to the present disclosure may be from about 5% to about 100%, as determined using ASTM D6866-10, method B. In other particular aspects, the bio-based content of the bio-based polyolefin may be from about 10% to about 100%, from about 25% to about 100%, from about 40% to about 100%, from about 50% to about 100%, from about 75% to about 100%, or from about 90% to about 100% and all ranges subsumed therein, as determined using ASTM D6866-10, method B. In other particular aspects, as described herein, one or more of the components of the absorbent article comprising one or more bio-based polyolefins may comprise a bio-based content of from about 5% to about 100%, from about 10% to about 100%, from about 25% to about 100%, from about 40% to about 100%, from about 50% to about 100%, from about 75% to about 100%, or from about 90% to about 100% and all ranges subsumed therein, as determined using ASTM D6866-10, method B. Polyolefins comprising a desired bio-based content may be obtained, for example, by mixing a conventional, i.e., petroleum-based, polyolefin with a bio-based polyolefin. In another embodiment, polyolefins comprising a desired bio-based content may be obtained, for example, by mixing a conventional, i.e., petroleum-based, polyolefin monomers with bio-based polyolefin monomers and then polymerizing the mixture.

One or more of the components of the absorbent articles according to the present disclosure may comprise, in addition to one or more polyolefins, one or more additional, optional materials, compounds, etc. (referred to collectively herein as "optional additives"), such as inorganic compounds, organic compounds, organic and inorganic fillers, pigments, dyes, antioxidants, UV-stabilizers, binders, surfactants, wetting agents, melt additives, incompatible polymers (e.g., polyester), miscible polymers, (different grades/types of polyolefins), dispersed polymers, and the like to impart desired properties, such as hydrophilic or hydrophobic properties, opacity, color tinting, flexibility, or other consumer benefit. For example, a polymeric film or fiber may be impregnated with an inorganic compound such as calcium carbonate, titanium dioxide, clays, silicas, zeolites, kaolin, mica, carbon, and mixtures thereof. Such compounds may serve as pore forming agents which, upon straining the film, may improve the breathability of the film. These additional materials and methods of use are described further in WO2016085711 and WO2016085709 and in U.S. Pat. Nos. 6,198,018; 6,677,258; and 9,241,843 and U.S. Pat. Appl. Pub. Nos. 2014/0378924; 2015/0173958; 2016/0114071; and 2016/0130731.

As described herein, the absorbent articles according to the present disclosure may comprise one or more of a topsheet, a backsheet comprising a backsheet film and a backsheet nonwoven web, a landing zone, a stretch or elastic ear film, a back ear nonwoven web, tape tabs, ear hooks, a front ear nonwoven web, a waist feature nonwoven web, waist feature elastics, a barrier leg cuff nonwoven web, outer leg elastics, an acquisition material, a core cover nonwoven web, belt elastics, a belt nonwoven web, chassis adhesives, or core adhesives, one or more of which may comprise one or more nonwoven materials or layers of nonwoven material, one or more films or layers of film, and/or composites, laminates, and/or other combinations thereof.

Reference is now made to individual components of an example absorbent article according to the present disclosure. The topsheet 26, 114 of the absorbent article may comprise a nonwoven topsheet, in which the nonwoven topsheet may comprise at least about 50% by weight of polyolefin. In some examples, the nonwoven topsheet may comprise at least about 75% by weight of polyolefin, at least about 95% by weight of polyolefin, or at least about 100% by weight of polyolefin. If the nonwoven topsheet does not comprise about 100% by weight of polyolefin, it may also comprise one or more of the optional additives listed above. In other examples, the nonwoven topsheet may comprise a bio-based polyolefin, in which a bio-based content of the bio-based polyolefin may be from about 5% to about 100%, as determined using ASTM D6866-10, method B. In further examples, the nonwoven topsheet may comprise a bio-based polyolefin with a bio-based content from about 10% to about 100%, from about 25% to about 100%, from about 40% to about 100%, from about 50% to about 100%, from about 75% to about 100%, or from about 90% to about 100%, and all ranges subsumed therein, as determined using ASTM D6866-10, method B. In some particular examples, the nonwoven topsheet comprising at least about 50% by weight, at least about 75% by weight, or at least about 95% by weight of polyolefin may comprise a bio-based polyolefin with a bio-based content from about 5% to about 100% using ASTM D6866-10, method B. The nonwoven topsheet may be formed, for example, from a single-layer nonwoven material as described herein. In some instances, the nonwoven topsheet may comprise an apertured nonwoven material. In other instances, the topsheet may comprise a laminate of a nonwoven material and a polymeric film. For example, the topsheet may comprise a laminate of apertured polyethylene film and a spunbond nonwoven material comprising polyethylene/polypropylene bicomponent fibers. In further instances, the topsheet may optionally comprise a secondary topsheet (not labeled), which may comprise higher gsm nonwoven polyolefin material.

The backsheet 28, 116 of the absorbent article may be joined to the topsheet. In some examples, the backsheet may comprise a bio-based polyolefin, in which a bio-based content of the bio-based polyolefin may be from about 5% to about 100%, as determined using ASTM D6866-10, method B. In other examples, the backsheet may comprise a bio-based polyolefin with a bio-based content from about 10% to about 100%, from about 25% to about 100%, from about 40% to about 100%, from about 50% to about 100%, from about 75% to about 100%, or from about 90% to about 100%, and all ranges subsumed therein, as determined using ASTM D6866-10, method B.

In some instances, the backsheet 28, 116 may comprise a backsheet film, in which the backsheet film may comprise at least about 50% by weight of polyolefin. In some examples, the backsheet film may comprise at least about 75% by weight of polyolefin, at least about 95% by weight of polyolefin, or at least about 100% by weight of polyolefin. If the backsheet film does not comprise about 100% by weight of polyolefin, it may also comprise one or more of the optional additives listed above. In other examples, the backsheet film may comprise a bio-based polyolefin, in which a bio-based content of the bio-based polyolefin may be from about 5% to about 100%, as determined using ASTM D6866-10, method B. In further examples, the backsheet film may comprise a bio-based polyolefin with a bio-based content from about 10% to about 100%, from about 25% to about 100%, from about 40% to about 100%, from about 50% to about 100%, from about 75% to about 100%, or from about 90% to about 100%, and all ranges subsumed therein, as determined using ASTM D6866-10, method B. In some particular examples, the backsheet film comprising at least about 50% by weight, at least about 75% by weight, or at least about 95% by weight of polyolefin may comprise a bio-based polyolefin with a bio-based content from about 5% to about 100% using ASTM D6866-10, method B. The backsheet film may be formed, for example, from a single-layer polymeric film as described herein. In some instances, the backsheet film may comprise a liquid impervious polyethylene film. In other instances, the backsheet may comprise one or more elastomeric films manufactured under the tradename VISTAMAXX® (ExxonMobil). As one particular example, the backsheet film may comprise a 0.5 to 1.0 mil (0.0005 to 0.001 inch) thick VISTAMAXX® elastomeric polypropylene film.

In other instances, the backsheet 28, 116 may comprise a backsheet nonwoven web (also referred to as an outer cover material 40), in which the backsheet nonwoven web may comprise at least about 50% by weight of polyolefin. In some examples, the backsheet nonwoven web may comprise at least about 75% by weight of polyolefin, at least about 95% by weight of polyolefin, or at least about 100% by weight of polyolefin. If the backsheet nonwoven web does not comprise about 100% by weight of polyolefin, it may also comprise one or more of the optional additives listed above. In other examples, the backsheet nonwoven web may comprise a bio-based polyolefin, in which a bio-based content of the bio-based polyolefin may be from about 5% to about 100%, as determined using ASTM D6866-10, method B. In further examples, the backsheet nonwoven web may comprise a bio-based polyolefin with a bio-based content from about 10% to about 100%, from about 25% to about 100%, from about 40% to about 100%, from about 50% to about 100%, from about 75% to about 100%, or from about 90% to about 100%, and all ranges subsumed therein, as determined using ASTM D6866-10, method B. In some particular examples, the backsheet nonwoven web comprising at least about 50% by weight, at least about 75% by weight, or at least about 95% by weight of polyolefin may comprise a bio-based polyolefin with a bio-based content from about 5% to about 100% using ASTM D6866-10, method B. The backsheet nonwoven web may be formed, for example, from a single-layer nonwoven material as described herein. The backsheet nonwoven web may comprise a soft, cloth-like material that is hydrophobic relative to the topsheet.

The absorbent article may further comprise a landing zone 44 formed from a nonwoven web or material or a laminate of a nonwoven material and a polymeric film, in which the landing zone comprises at least about 50% by weight of polyolefin. In some examples, the landing zone may comprise at least about 75% by weight of polyolefin, at least about 95% by weight of polyolefin, or at least about 100% by weight of polyolefin. If the landing zone does not comprise about 100% by weight of polyolefin, it may also comprise one or more of the optional additives listed above. In other examples, the landing zone may comprise a bio-based polyolefin, in which a bio-based content of the bio-based polyolefin may be from about 5% to about 100%, as determined using ASTM D6866-10, method B. In further examples, the landing zone may comprise a bio-based polyolefin with a bio-based content from about 10% to about 100%, from about 25% to about 100%, from about 40% to about 100%, from about 50% to about 100%, from about 75% to about 100%, or from about 90% to about 100%, and all ranges subsumed therein, as determined using ASTM D6866-10, method B. In some particular examples, the landing zone comprising at least about 50% by weight, at least about 75% by weight, or at least about 95% by weight of polyolefin may comprise a bio-based polyolefin with a bio-based content from about 5% to about 100% using ASTM D6866-10, method B.

The absorbent article may further comprise one or more pairs of ears. The one or more pairs of ears may comprise back ears 42, which may comprise a back ear nonwoven web, in which the back ear nonwoven web may comprise at least about 50% by weight of polyolefin. In some examples, the back ear nonwoven web may comprise at least about 75% by weight of polyolefin, at least about 95% by weight of polyolefin, or at least about 100% by weight of polyolefin. If the back ear nonwoven web does not comprise about 100% by weight of polyolefin, it may also comprise one or more of the optional additives listed above. In other examples, the back ear nonwoven web may comprise a bio-based polyolefin, in which a bio-based content of the bio-based polyolefin may be from about 5% to about 100%, as determined using ASTM D6866-10, method B. In further examples, the back ear nonwoven web may comprise a bio-based polyolefin with a bio-based content from about 10% to about 100%, from about 25% to about 100%, from about 40% to about 100%, from about 50% to about 100%, from about 75% to about 100%, or from about 90% to about 100%, and all ranges subsumed therein, as determined using ASTM D6866-10, method B. In some particular examples, the back ear nonwoven web comprising at least about 50% by weight, at least about 75% by weight, or at least about 95% by weight of polyolefin may comprise a bio-based polyolefin with a bio-based content from about 5% to about 100% using ASTM D6866-10, method B.

The one or more pairs of ears may comprise front ears 47, which may comprise a front ear nonwoven web that is generally non-elastic. The front ear nonwoven web may comprise at least about 50% by weight of polyolefin. In some examples, the front ear nonwoven web may comprise at least about 75% by weight of polyolefin, at least about 95% by weight of polyolefin, or at least about 100% by weight of polyolefin. If the front ear nonwoven web does not comprise about 100% by weight of polyolefin, it may also comprise one or more of the optional additives listed above. In other examples, the front ear nonwoven web may comprise a bio-based polyolefin, in which a bio-based content of the bio-based polyolefin may be from about 5% to about 100%, as determined using ASTM D6866-10, method B. In further examples, the front ear nonwoven web may comprise a bio-based polyolefin with a bio-based content from about 10% to about 100%, from about 25% to about 100%, from about 40% to about 100%, from about 50% to about 100%, from about 75% to about 100%, or from about 90% to about 100%, and all ranges subsumed therein, as determined using ASTM D6866-10, method B. In some particular examples, the front ear nonwoven web comprising at least about 50% by weight, at least about 75% by weight, or at least about 95% by weight of polyolefin may comprise a bio-based polyolefin with a bio-based content from about 5% to about 100% using ASTM D6866-10, method B.

One or more of the pairs of ears, e.g., the back ears 42, may comprise a stretch or elastic ear film or elastic strands, in which the stretch or elastic ear film or strands may comprise at least about 50% by weight of polyolefin. In some examples, the stretch or elastic ear film or strands may comprise at least about 75% by weight of polyolefin, at least about 95% by weight of polyolefin, or at least about 100% by weight of polyolefin. If the stretch or elastic ear film or strands does not comprise about 100% by weight of polyolefin, it may also comprise one or more of the optional additives listed above. In other examples, the stretch or elastic ear film or strands may comprise a bio-based polyolefin, in which a bio-based content of the bio-based polyolefin may be from about 5% to about 100%, as determined using ASTM D6866-10, method B. In further examples, the stretch or elastic ear film or strands may comprise a bio-based polyolefin with a bio-based content from about 10% to about 100%, from about 25% to about 100%, from about 40% to about 100%, from about 50% to about 100%, from about 75% to about 100%, or from about 90% to about 100%, and all ranges subsumed therein, as determined using ASTM D6866-10, method B. In some particular examples, the stretch or elastic ear film or strands comprising at least about 50% by weight, at least about 75% by weight, or at least about 95% by weight of polyolefin may comprise a bio-based polyolefin with a bio-based content from about 5% to about 100% using ASTM D6866-10, method B.

One or more of the pairs of ears, e.g., the back ears 42, may comprise ear hooks, e.g., fasteners 46, in which the ear hooks may comprise at least about 50% by weight of polyolefin. In some examples, the ear hooks may comprise at least about 75% by weight of polyolefin, at least about 95% by weight of polyolefin, or at least about 100% by weight of polyolefin. If the ear hooks do not comprise about 100% by weight of polyolefin, they may also comprise one or more of the optional additives listed above. In other examples, the ear hooks may comprise a bio-based polyolefin, in which a bio-based content of the bio-based polyolefin may be from about 5% to about 100%, as determined using ASTM D6866-10, method B. In further examples, the ear hooks may comprise a bio-based polyolefin with a bio-based content from about 10% to about 100%, from about 25% to about 100%, from about 40% to about 100%, from about 50% to about 100%, from about 75% to about 100%, or from about 90% to about 100%, and all ranges subsumed therein, as determined using ASTM D6866-10, method B. In some particular examples, the ear hooks comprising at least about 50% by weight, at least about 75% by weight, or at least about 95% by weight of polyolefin may comprise a bio-based polyolefin with a bio-based content from about 5% to about 100% using ASTM D6866-10, method B. The ear hooks may be formed from a polymer comprising one or more polyolefins and may be configured to engage and lock with a plurality of loops located, for example, on the landing zone.

One of more of the pairs of ears, e.g., the back ears 42, may comprise tape tabs 43, in which the tape tabs 43 may comprise at least about 50% by weight of polyolefin. In some examples, the tape tabs 43 may comprise at least about 75% by weight of polyolefin, at least about 95% by weight of polyolefin, or at least about 100% by weight of polyolefin. If the tape tabs 43 do not comprise about 100% by weight of polyolefin, they may also comprise one or more of the optional additives listed above. In other examples, the tape tabs may comprise a bio-based polyolefin, in which a bio-based content of the bio-based polyolefin may be from about 5% to about 100%, as determined using ASTM D6866-10, method B. In further examples, the tape tabs may comprise a bio-based polyolefin with a bio-based content from about 10% to about 100%, from about 25% to about 100%, from about 40% to about 100%, from about 50% to about 100%, from about 75% to about 100%, or from about 90% to about 100%, and all ranges subsumed therein, as determined using ASTM D6866-10, method B. In some particular examples, the tape tabs comprising at least about 50% by weight, at least about 75% by weight, or at least about 95% by weight of polyolefin may comprise a bio-based polyolefin with a bio-based content from about 5% to about 100% using ASTM D6866-10, method B.

The absorbent article may further comprise one or more waistbands, e.g., elastic waistbands 36, which may comprise a waist feature nonwoven web comprising one or more layers of nonwoven web. The one or more layers of nonwoven web may comprise at least about 50% by weight of polyolefin. In some examples, the one or more layers of nonwoven web may comprise at least about 75% by weight of polyolefin, at least about 95% by weight of polyolefin, or at least about 100% by weight of polyolefin. If the one or more layers of nonwoven web do not comprise about 100% by weight of polyolefin, it may also comprise one or more of the optional additives listed above. In other examples, the one or more layers of nonwoven web may comprise a bio-based polyolefin, in which a bio-based content of the bio-based polyolefin may be from about 5% to about 100%, as determined using ASTM D6866-10, method B. In further examples, the one or more layers of nonwoven web may comprise a bio-based polyolefin with a bio-based content from about 10% to about 100%, from about 25% to about 100%, from about 40% to about 100%, from about 50% to about 100%, from about 75% to about 100%, or from about 90% to about 100%, and all ranges subsumed therein, as determined using ASTM D6866-10, method B. In some particular examples, the one or more layers of nonwoven web comprising at least about 50% by weight, at least about 75% by weight, or at least about 95% by weight of polyolefin may comprise a bio-based polyolefin with a bio-based content from about 5% to about 100% using ASTM D6866-10, method B.

In some examples, the waistband(s) may further comprise waist feature elastics, such as an elastic film or elastic strands, in which the waist feature elastics may comprise at least about 50% by weight of polyolefin. In some particular examples, the waist feature elastics may comprise at least about 75% by weight of polyolefin, at least about 95% by weight of polyolefin, or at least about 100% by weight of polyolefin. If the waist feature elastics do not comprise about 100% by weight of polyolefin, they may also comprise one or more of the optional additives listed above. In some examples, the waist feature elastics may comprise a bio-based polyolefin, in which a bio-based content of the bio-based polyolefin may be from about 5% to about 100%, as determined using ASTM D6866-10, method B. In further examples, the waist feature elastics may comprise a bio-based polyolefin with a bio-based content from about 10% to about 100%, from about 25% to about 100%, from about 40% to about 100%, from about 50% to about 100%, from about 75% to about 100%, or from about 90% to about 100%, and all ranges subsumed therein, as determined using ASTM D6866-10, method B. In some particular examples, the waist feature elastics comprising at least about 50% by weight, at least about 75% by weight, or at least about 95% by weight of polyolefin may comprise a bio-based polyolefin with a bio-based content from about 5% to about 100% using ASTM D6866-10, method B.

The absorbent article may further comprise one or more belts, e.g., front and back belts 54, 56, each of which may comprise a belt nonwoven web comprising one or more layers of nonwoven web. The one or more layers of nonwoven web may comprise at least about 50% by weight of polyolefin. In some examples, the one or more layers of nonwoven web may comprise at least about 75% by weight of polyolefin, at least about 95% by weight of polyolefin, or at least about 100% by weight of polyolefin. If the one or more layers of nonwoven web do not comprise about 100% by weight of polyolefin, it may also comprise one or more of the optional additives listed above. In other examples, the one or more layers of nonwoven web may comprise a bio-based polyolefin, in which a bio-based content of the bio-based polyolefin may be from about 5% to about 100%, as determined using ASTM D6866-10, method B. In further examples, the one or more layers of nonwoven web may comprise a bio-based polyolefin with a bio-based content from about 10% to about 100%, from about 25% to about 100%, from about 40% to about 100%, from about 50% to about 100%, from about 75% to about 100%, or from about 90% to about 100%, and all ranges subsumed therein, as determined using ASTM D6866-10, method B. In some particular examples, the one or more layers of nonwoven web comprising at least about 50% by weight, at least about 75% by weight, or at least about 95% by weight of polyolefin may comprise a bio-based polyolefin with a bio-based content from about 5% to about 100% using ASTM D6866-10, method B.

In some examples, the one or more belts 54, 56 may also comprise belt elastics, e.g., elastic strands 68 or a film, in which the belt elastics may comprise at least about 50% by weight of polyolefin. In some particular examples, the belt elastics may comprise at least about 75% by weight of polyolefin, at least about 95% by weight of polyolefin, or at least about 100% by weight of polyolefin. If the belt elastics do not comprise about 100% by weight of polyolefin, they may also comprise one or more of the optional additives listed above. In other examples, the belt elastics may comprise a bio-based polyolefin, in which a bio-based content of the bio-based polyolefin may be from about 5% to about 100%, as determined using ASTM D6866-10, method B. In further examples, the belt elastics may comprise a bio-based polyolefin with a bio-based content from about 10% to about 100%, from about 25% to about 100%, from about 40% to about 100%, from about 50% to about 100%, from about 75% to about 100%, or from about 90% to about 100%, and all ranges subsumed therein, as determined using ASTM D6866-10, method B. In some particular examples, the belt elastics comprising at least about 50% by weight, at least about 75% by weight, or at least about 95% by weight of polyolefin may comprise a bio-based polyolefin with a bio-based content from about 5% to about 100% using ASTM D6866-10, method B.

The absorbent article may further comprise one or more pairs of barrier leg cuffs 32, which may comprise a barrier leg cuff nonwoven web and one or more elastics 33, e.g., elastic strands or strips. The barrier leg cuff nonwoven web may comprise at least about 50% by weight of polyolefin. In some examples, the barrier leg cuff nonwoven web may comprise at least about 75% by weight of polyolefin, at least about 95% by weight of polyolefin, or at least about 100% by weight of polyolefin. If the barrier leg cuff nonwoven web does not comprise about 100% by weight of polyolefin, it may also comprise one or more of the optional additives listed above. In other examples, the barrier leg cuff nonwoven web may comprise a bio-based polyolefin, in which a bio-based content of the bio-based polyolefin may be from about 5% to about 100%, as determined using ASTM D6866-10, method B. In further examples, the barrier leg cuff nonwoven web may comprise a bio-based polyolefin with a bio-based content from about 10% to about 100%, from about 25% to about 100%, from about 40% to about 100%, from about 50% to about 100%, from about 75% to about 100%, or from about 90% to about 100%, and all ranges subsumed therein, as determined using ASTM D6866-10, method B. In some particular examples, the barrier leg cuffs comprising at least about 50% by weight, at least about 75% by weight, or at least about 95% by weight of polyolefin may comprise a bio-based polyolefin with a bio-based content from about 5% to about 100% using ASTM D6866-10, method B.

The barrier leg cuff elastics 33 may comprise at least about 50% by weight of polyolefin. In some examples, the barrier leg cuff elastics may comprise at least about 75% by weight of polyolefin, at least about 95% by weight of polyolefin, or at least about 100% by weight of polyolefin. If the barrier leg cuff elastics do not comprise about 100% by weight of polyolefin, they may also comprise one or more of the optional additives listed above. In other examples, the barrier leg cuff elastics may comprise a bio-based polyolefin, in which a bio-based content of the bio-based polyolefin may be from about 5% to about 100%, as determined using ASTM D6866-10, method B. In further examples, the barrier leg cuff elastics may comprise a bio-based polyolefin with a bio-based content from about 10% to about 100%, from about 25% to about 100%, from about 40% to about 100%, from about 50% to about 100%, from about 75% to about 100%, or from about 90% to about 100%, and all ranges subsumed therein, as determined using ASTM D6866-10, method B. In some particular examples, the barrier leg cuff elastics comprising at least about 50% by weight, at least about 75% by weight, or at least about 95% by weight of polyolefin may comprise a bio-based polyolefin with a bio-based content from about 5% to about 100% using ASTM D6866-10, method B.

The absorbent article may further comprise outer leg elastics 34, in which the outer leg elastics 34 may comprise at least about 50% by weight of polyolefin. In some examples, the outer leg elastics may comprise at least about 75% by weight of polyolefin, at least about 95% by weight of polyolefin, or at least about 100% by weight of polyolefin. If the outer leg elastics do not comprise about 100% by weight of polyolefin, they may also comprise one or more of the optional additives listed above. In other examples, the outer leg elastics may comprise a bio-based polyolefin, in which a bio-based content of the bio-based polyolefin may be from about 5% to about 100%, as determined using ASTM D6866-10, method B. In further examples, the outer leg elastics may comprise a bio-based polyolefin with a bio-based content from about 10% to about 100%, from about 25% to about 100%, from about 40% to about 100%, from about 50% to about 100%, from about 75% to about 100%, or from about 90% to about 100%, and all ranges subsumed therein, as determined using ASTM D6866-10, method B. In some particular examples, the outer leg elastics comprising at least about 50% by weight, at least about 75% by weight, or at least about 95% by weight of polyolefin may comprise a bio-based polyolefin with a bio-based content from about 5% to about 100% using ASTM D6866-10, method B.

Additional examples of nonwoven materials, films, and elastic materials for forming the waistband(s), belt(s), barrier leg cuffs, and/or outer leg elastics of an absorbent article according to the present disclosure are discussed in U.S. Pat. Appl. Pub. Nos. 2016/0074250 and 2016/0136014.

The absorbent article may further comprise one or more acquisition materials 38, in which the acquisition material may comprise at least about 50% by weight of polyolefin. In some examples, the acquisition material may comprise at least about 75% by weight of polyolefin, at least about 95% by weight of polyolefin, or at least about 100% by weight of polyolefin. If the acquisition material does not comprise about 100% by weight of polyolefin, it may also comprise one or more of the optional additives listed above. In other examples, the acquisition material may comprise a bio-based polyolefin, in which a bio-based content of the bio-based polyolefin may be from about 5% to about 100%, as determined using ASTM D6866-10, method B. In further examples, the acquisition material may comprise a bio-based polyolefin with a bio-based content from about 10% to about 100%, from about 25% to about 100%, from about 40% to about 100%, from about 50% to about 100%, from about 75% to about 100%, or from about 90% to about 100%, and all ranges subsumed therein, as determined using ASTM D6866-10, method B. In some particular examples, the acquisition material comprising at least about 50% by weight, at least about 75% by weight, or at least about 95% by weight of polyolefin may comprise a bio-based polyolefin with a bio-based content from about 5% to about 100% using ASTM D6866-10, method B. The acquisition material may comprise, for example, polyolefin fibers or filaments or a polyolefinic nonwoven material with a suitable binder. In some instances, the absorbent article may comprise an acquisition material that is positioned intermediate the topsheet and the absorbent core, in which the absorbent core is positioned intermediate the acquisition material and the backsheet. Additional examples of materials for forming the acquisition material of an absorbent article according to the present disclosure are discussed in U.S. Pat. Nos. 5,304,161 and 5,439,458.

The absorbent core may comprise a core cover, e.g., the core wrap 74, that comprises a core cover nonwoven web, in which the core cover nonwoven web may comprise at least about 50% by weight of polyolefin. In some examples, the core cover nonwoven web may comprise at least about 75% by weight of polyolefin, at least about 95% by weight of polyolefin, or at least about 100% by weight of polyolefin. If the core cover does not comprise about 100% by weight of polyolefin, it may also comprise one or more of the optional additives listed above. In other examples, the core cover may comprise a bio-based polyolefin, in which a bio-based content of the bio-based polyolefin may be from about 5% to about 100%, as determined using ASTM D6866-10, method B. In further examples, the core cover may comprise a bio-based polyolefin with a bio-based content from about 10% to about 100%, from about 25% to about 100%, from about 40% to about 100%, from about 50% to about 100%, from about 75% to about 100%, or from about 90% to about 100%, and all ranges subsumed therein, as determined using ASTM D6866-10, method B. In some particular examples, the core cover comprising at least about 50% by weight, at least about 75% by weight, or at least about 95% by weight of polyolefin may comprise a bio-based polyolefin with a bio-based content from about 5% to about 100% using ASTM D6866-10, method B. Additional examples of nonwoven materials for forming the core cover of an absorbent article according to the present disclosure are discussed in U.S. Pat. No. 8,785,716.

The absorbent article may comprise one or more glues or adhesives that may be used to join one or more of the components of the absorbent article. The adhesives may optionally be used between the layers of a laminate to increase the bond strength between the laminate materials. In some aspects, the one or more adhesives may comprise chassis adhesives that may be used to join: the topsheet 26, 114 to one or more of the acquisition material 38, the absorbent core 30, the backsheet 28, 116 (i.e., the backsheet film), the barrier leg cuffs 32, or the outer leg elastics 34; the barrier leg cuff elastics 33 to the barrier leg cuff nonwoven web; the backsheet 28, 116 to one or more of the topsheet 26, 114, the outer cover material 40, or the absorbent core 30; the one or more elastic waistbands 36 to the topsheet 26, 114; the front and back ears 47, 42 to one of the topsheet 26, 114, the backsheet 28, 116, or the outer cover material 40; the back ear nonwoven web(s) and the stretch or elastic ear film or strands; and/or the landing zone 44 to the outer cover material 40. In some examples, the barrier leg cuff nonwoven web may be bonded via one or more chassis adhesives to the absorbent article 10, e.g., the topsheet, so that the barrier leg cuffs 32 extend upwards from the wearer-facing surface 4 of the absorbent article 10. In some particular aspects, one or more chassis adhesives may be used to join the chassis 52 to a wearer-facing surface 4 of the front and back belts 54, 56 or to a garment-facing surface 2 of the belts 54, 56. In other aspects, the one or more adhesives of the absorbent article may comprise core adhesives that may be used, for example, to immobilize the superabsorbent polymer particles within the core wrap 74.

In some examples, the chassis and/or core adhesives may comprise at least about 50% by weight of polyolefin. In some particular examples, the chassis and/or core adhesives may comprise at least about 75% by weight of polyolefin, at least about 95% by weight of polyolefin, or at least about 100% by weight of polyolefin. If the chassis and/or core adhesives do not comprise about 100% by weight of polyolefin, they may also comprise one or more of the optional additives listed above or any of the additives set out in U.S. Pat. No. 9,241,843 and U.S. Pat. Appl. Pub. Nos. 2014/0378924 and 2015/0173958. In other examples, the chassis and/or core adhesives may comprise a bio-based polyolefin, in which a bio-based content of the bio-based polyolefin may be from about 5% to about 100%, as determined using ASTM D6866-10, method B. In further examples, the chassis and/or core adhesives may comprise a bio-based polyolefin with a bio-based content from about 10% to about 100%, from about 25% to about 100%, from about 40% to about 100%, from about 50% to about 100%, from about 75% to about 100%, or from about 90% to about 100%, and all ranges subsumed therein, as determined using ASTM D6866-10, method B. In some particular examples, the chassis and/or core adhesives comprising at least about 50% by weight, at least about 75% by weight, or at least about 95% by weight of polyolefin may comprise a bio-based polyolefin with a bio-based content from about 5% to about 100% using ASTM D6866-10, method B.

In addition to or in place of the core and/or chassis adhesives, the components and/or layers of the absorbent articles according to the present disclosure may be joined together by other non-adhesive attachment methods known to those of skill in the art. For example, the components and/or layers of the absorbent article may be joined by one or more of pressure bonding, heat bonding, ultrasonic bonding, or embossing.

Recycling of Absorbent Articles Comprising Recyclable Materials

Following use, absorbent articles comprising one or more recyclable materials according to the present disclosure may be prepared for recycling using one or more known methods. Exemplary methods for treatment of absorbent articles for recycling are described in, for example, U.S. Pat. Nos. 8,883,076; 8,979,005; 9,095,853; and 9,156,034. These exemplary methods may be used, for example, to open folded absorbent articles and to dry, sterilize, and at least partially destructure the absorbent articles.

In accordance with the present disclosure, an absorbent article comprising a topsheet, a backsheet joined to the topsheet, and an absorbent core comprising a core absorbent material may comprise a polyolefin content of at least about 90% by weight, based on a total weight of the absorbent article excluding the core absorbent material. In another example, in an absorbent article comprising 17 enumerated components as discussed above, at least 13 of the 17 enumerated components may comprise polyolefins, and in some particular examples, at least 14 or at least 15 or at least 16 of the 17 enumerated components of the absorbent article may comprise polyolefins. In a further example, in an absorbent article comprising 11 enumerated components as discussed above, at least 7 of the 11 enumerated components may comprise polyolefins, and in some particular examples, at least 8 or at least 9 or at least 10 of the 11 enumerated components of the absorbent article may comprise polyolefins.

Hence, the absorbent articles according to the present disclosure primarily comprise two materials: polyolefins and an absorbent core material. Used absorbent articles according to the present disclosure may be recycled. Because the absorbent articles according to the present disclosure primarily comprise only two materials, it is believed that recycling processes for recycling the used absorbent articles can be simplified and made more efficient as the number of different materials that must be separated from one another is minimized. For example, absorbent articles according to the present disclosure may be separated into two components, e.g., polyolefin plastic scrap and the absorbent core material (e.g., the superabsorbent polymers), using one or more recycling operations as described above, in which each component is of high purity.

REPRESENTATIVE EXAMPLES

It is believed that an example absorbent article according to the present disclosure may comprise the following 17 enumerated components: (1) a topsheet; (2) a backsheet film; (3) a backsheet nonwoven web; (4) a landing zone; (5) a stretch ear film; (6) a back ear nonwoven web; (7) tape tabs; (8) ear hooks; (9) a front ear nonwoven web; (10) a waist feature nonwoven web; (11) waist feature elastics; (12) a barrier leg cuff nonwoven web; (13) outer leg elastics; (14) an acquisition material; (15) a core cover nonwoven web; (16) chassis adhesives; and (17) core adhesives.

In one particular example, it is believed that an absorbent article may comprise the same 17 enumerated components, in which at least 13 of the 17 enumerated components of the absorbent article comprise one or more polyolefins. For example, the topsheet, the backsheet film, the backsheet nonwoven web, the landing zone, the stretch ear film, the back ear nonwoven web, the tape tabs, the ear hooks, the front ear nonwoven web, the waist feature nonwoven web, the barrier leg cuff nonwoven web, the acquisition material, and the core cover nonwoven web may comprise one or more polyolefins.

In another particular example, it is believed that an absorbent article may comprise the same 17 enumerated components, wherein at least 14 of the 17 enumerated components of the absorbent article comprise one or more polyolefins. For example, the topsheet, the backsheet film, the backsheet nonwoven web, the landing zone, the stretch ear film, the back ear nonwoven web, the tape tabs, the ear hooks, the front ear nonwoven web, the waist feature nonwoven web, the barrier leg cuff nonwoven web, the acquisition material, the core cover nonwoven web, and the core adhesives may comprise one or more polyolefins.

In yet another particular example, it is believed that an absorbent article may comprise the same 17 enumerated components, wherein at least 15 of the 17 enumerated components of the absorbent article comprise one or more polyolefins. For example, the topsheet, the backsheet film, the backsheet nonwoven web, the landing zone, the stretch ear film, the back ear nonwoven web, the tape tabs, the ear hooks, the front ear nonwoven web, the waist feature nonwoven web, the barrier leg cuff nonwoven web, the acquisition material, the core cover nonwoven web, the core adhesives, and the chassis adhesives may comprise one or more polyolefins.

In yet another particular example, it is believed that an absorbent article may comprise the same 17 enumerated components, wherein at least 16 of the 17 enumerated components of the absorbent article comprise one or more polyolefins. For example, the topsheet, the backsheet film, the backsheet nonwoven web, the landing zone, the stretch ear film, the back ear nonwoven web, the tape tabs, the ear hooks, the front ear nonwoven web, the waist feature nonwoven web, the barrier leg cuff nonwoven web, the acquisition material, the core cover nonwoven web, the core adhesives, the chassis adhesives, and the outer leg elastics may comprise one or more polyolefins.

It is believed that another example absorbent article according to the present disclosure may comprise the following 11 enumerated components: (1) a topsheet; (2) a backsheet film; (3) a backsheet nonwoven web; (4) belt elastics; (5) a belt nonwoven web; (6) chassis adhesives; (7) a barrier leg cuff nonwoven web; (8) outer leg elastics; (9) an acquisition material; (10) a core cover nonwoven web; and (11) core adhesives. This example absorbent article may be in the form of a pant as described herein.

In one particular example, it is believed that an absorbent article may comprise the same 11 enumerated components, and wherein at least 7 of the 11 enumerated components of the absorbent article comprise one or more polyolefins. For example, the topsheet, the backsheet film, the backsheet nonwoven web, the belt nonwoven web, the barrier leg cuff nonwoven web, the acquisition material, and the core cover nonwoven web may comprise one or more polyolefins.

In another particular example, it is believed that an absorbent article may comprise the same 11 enumerated components, and wherein at least 8 of the 11 enumerated components of the absorbent article comprise one or more polyolefins. For example, the topsheet, the backsheet film, the backsheet nonwoven web, the belt nonwoven web, the barrier leg cuff nonwoven web, the acquisition material, the core cover nonwoven web, and the chassis adhesives may comprise one or more polyolefins.

In yet another particular example, it is believed that an absorbent article may comprise the same 11 enumerated components, and wherein at least 9 of the 11 enumerated components of the absorbent article comprise one or more polyolefins. For example, the topsheet, the backsheet film, the backsheet nonwoven web, the belt nonwoven web, the barrier leg cuff nonwoven web, the acquisition material, the core cover nonwoven web, the chassis adhesives, and the core adhesives may comprise one or more polyolefins.

In yet another particular example, it is believed that an absorbent article may comprise the same 11 enumerated components, and wherein at least 10 of the 11 enumerated components of the absorbent article comprise one or more polyolefins. For example, the topsheet, the backsheet film, the backsheet nonwoven web, the belt nonwoven web, the barrier leg cuff nonwoven web, the acquisition material, the core cover nonwoven web, the chassis adhesives, the core adhesives, and the outer leg elastics may comprise one or more polyolefins.

It is believed that one or more of the enumerated components of any of these example absorbent articles that comprise one or more polyolefins may comprise at least about 50% by weight of polyolefin. In other examples, it is believed that one or more of the components of these example absorbent articles that comprise one or more polyolefins may comprise at least about 75% by weight of polyolefin. In further particular examples, it is believed that one or more of the components of these example absorbent articles that comprise one or more polyolefins may comprise at least about 95% by weight of polyolefin. These example absorbent articles may be disposable.

It is believed that all of these example absorbent articles may comprise a structure in which the topsheet is joined to a backsheet defined by the backsheet film and the backsheet nonwoven web; the core cover nonwoven web and a core absorbent material are positioned intermediate the topsheet and the backsheet; and the core absorbent material comprises superabsorbent polymers with a bio-based content from about 5% to about 100% using ASTM D6866-10, method B. It is believed that the core absorbent material in all of these example absorbent articles may comprise superabsorbent polymers with a bio-based content from about 10% to about 100%, from about 25% to about 100%, from about 40% to about 100%, from about 50% to about 100%, from about 75% to about 100%, from about 90% to about 100%, and all ranges subsumed therein, using ASTM D6866-10, method B.

In further aspects, it is believed that at least one of the enumerated components of any of these example absorbent articles that comprises one or more polyolefins may comprise a bio-based polyolefin with a bio-based content from about 5% to about 100%, as determined using ASTM D6866-10, method B. In yet further aspects, it is believed that at least one of the enumerated components of any of these example absorbent articles that comprises one or more polyolefins may comprise a bio-based polyolefin with a bio-based content from about 10% to about 100%, from about 25% to about 100%, from about 40% to about 100%, from about 50% to about 100%, from about 75% to about 100%, from about 90% to about 100%, and all ranges subsumed therein, using ASTM D6866-10, method B.

Test Methods

Method to Evaluate the Olefin Content of an Absorbent Article

This method may be used to determine: (1) the olefin content of an individual component harvested from an absorbent article; and (2) the overall olefin content of an absorbent article comprising the individual harvested components.

The absorbent article is to be deconstructed, removing the core materials, and separating each of the other structures into distinctive individual components. The components are weighed and analyzed using the following standard methods: (1) Differential Scanning Calorimetry (DSC) (ASTM D3418.21296); and (2) FT (Fourier transformed) Infrared Spectroscopy with ATR (Attenuated total reflection) (ASTM E1252.29254).

Unless otherwise specified, all tests described herein, including those described in the detailed description, are conducted on samples that have been conditioned in a conditioned room at a temperature of 73° F.±2° F. (23° C.±1° C.) and a relative humidity of 50% (±2%) for 2 hours prior to the test. All tests are conducted in such conditioned room(s).

Sample Preparation

The absorbent article is deconstructed into the individual components, and residual adhesive on each component is removed via dissolution in any suitable solvent, for example, Tetrahydrofuran (THF)—Stabilized (HPLC Grade). The components are air-dried for 30 minutes to remove traces of solvent. The weight of each individual component is recorded in gram (g) to the nearest 0.01 g. The steps in harvesting the components are shown below:

Procedure

1. Obtain a 3-4 liter beaker;
2. Obtain one 4 liter bottle of solvent;
3. In a hood, transfer 1 liter of solvent into the 3-4 liter beaker;
4. Apply C-clamps to the top and bottom of the absorbent article;
5. Take one absorbent article and submerge in the 1 liter of solvent;
6. Place beaker on shaking table and stir gently for 15 minutes;
7. Let solution with the absorbent article sit for 5 additional minutes;
8. Take the absorbent article out of solvent solution;
9. Carefully squeeze solvent solution out of the absorbent article;
10. Place the absorbent article on a glass dish (topsheet side up);
11. Carefully dissemble product, take note of the order of the components;
12. Place components on racks in hood and insure correct ID of components;
13. Let components air dry in hood for a minimum of 15 minutes;
14. Once components are completely dry, proceed with dimensional analysis; and
15. Record the weight and the physical dimensions of each of the individual materials.

Sampling

For the DSC from each component a sample is cut not exceeding 3 mm in diameter. For the ATR FT IR a sample sufficient in size to cover the IR crystal is cut.

Analysis

Each component is then analyzed by Differential Scanning Calorimetry (ASTM D3418.21296) and FT (Fourier transformed) Infrared Spectroscopy with ATR (Attenuated total reflection) (ASTM E1252.29254). The resulting thermograms and FTIR spectra are evaluated to determine the percentage of the component specimen consistent with an olefin. The comparison of the melting peak area of the second heat in the DSC will provide the ratio of olefin to non-olefinic material in the individual component.

Result

The percentage olefin content of each individual component of the absorbent article multiplied by its mass are combined and then divided by the total weight of the article minus the weight of the absorbent material to yield the overall olefin percentage of the article. The individual components olefin percentage and the overall olefin percentage is reported to the nearest 1%.

The In-Bag Stack Height of a Package of Articles:

A thickness tester with a flat, rigid horizontal sliding plate is used. The thickness tester is configured so that the horizontal sliding plate moves freely in a vertical direction with the horizontal sliding plate always maintained in a horizontal orientation directly above a flat, rigid horizontal base plate. The thickness tester includes a suitable device for measuring the gap between the horizontal sliding plate and the horizontal base plate to within ±0.5 mm. The horizontal sliding plate and the horizontal base plate are larger than the surface of the absorbent article package that contacts each plate, i.e., each plate extends past the contact surface of the absorbent article package in all directions. The horizontal sliding plate exerts a downward force of 850±1 gram-force (8.34 N) on the absorbent article package, which may be achieved by placing a suitable weight on the center of the non-package-contacting top surface of the horizontal sliding plate so that the total mass of the sliding plate plus added weight is 850±1 grams.

Absorbent article packages are equilibrated at 23±2° C. and 50±5% relative humidity prior to measurement.

The horizontal sliding plate is raised and an absorbent article package is placed centrally under the horizontal sliding plate in such a way that the absorbent articles within the package are in a horizontal orientation (see FIG. 16). Any handle or other packaging feature on the surfaces of the package that would contact either of the plates is folded flat against the surface of the package so as to minimize their impact on the measurement. The horizontal sliding plate is lowered slowly until it contacts the top surface of the package and then released. The gap between the horizontal plates is measured to within ±0.5 mm ten seconds after releasing the horizontal sliding plate. Five identical packages (same size packages and same absorbent articles counts) are measured and the arithmetic mean is reported as the package width. The "In-Bag Stack Height"=(package width/absorbent article count per stack)×10 is calculated and reported to within ±0.5 mm.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising:
   a topsheet;
   a backsheet joined to the topsheet and comprising one or more of a backsheet film or a backsheet nonwoven web;
   an absorbent core positioned intermediate the topsheet and the backsheet, the absorbent core comprising a core absorbent material; and
   one or more of a landing zone, a stretch ear film, a back ear nonwoven web, tape tabs, ear hooks, a front ear nonwoven web, a waist feature nonwoven web, waist feature elastics, a barrier leg cuff nonwoven web, outer leg elastics, an acquisition material, a core cover nonwoven web, chassis adhesives, or core adhesives;
   wherein the core absorbent material comprises superabsorbent polymers with a bio-based content from about 5% to about 100% using ASTM D6866-10, method B;
   wherein at least one of the topsheet or the backsheet and at least one of the backsheet film, the backsheet nonwoven web, the landing zone, the stretch ear film, the back ear nonwoven web, the tape tabs, the ear hooks, the front ear nonwoven web, the waist feature nonwoven web, the waist feature elastics, the barrier leg cuff nonwoven web, the outer leg elastics, the acquisition material, the core cover nonwoven web, the chassis adhesives, or the core adhesives comprise a bio-based polyolefin with:
      a bio-based content from 5% to 100% using ASTM D6866-10, method B; and
      a purity of about 98 weight % polyolefin and less than 2 weight % impurities; and
   wherein the absorbent article comprises a polyolefin content of at least about 90% by weight, based on a total weight of the absorbent article excluding the core absorbent material; and
   wherein recycled polyolefin recovered from an entirety of the absorbent article via a recycling operation comprises a polyolefin content of at least about 90% by weight, based on a total weight of the absorbent article excluding the core absorbent material.

2. The absorbent article of claim 1, wherein the polyolefin content comprises at least about 95% by weight, based on the total weight of the absorbent article excluding the core absorbent material.

3. The absorbent article of claim 1, wherein the polyolefin content comprises at least about 99% by weight, based on the total weight of the absorbent article excluding the core absorbent material.

4. The absorbent article of claim 1, wherein the bio-based content of the superabsorbent polymers comprises from about 10% to about 100% using ASTM D6866-10, method B.

5. The absorbent article of claim 1, wherein the bio-based content of the superabsorbent polymers comprises from about 90% to about 100% using ASTM D6866-10, method B.

6. The absorbent article of claim 1, wherein the at least one of the nonwoven topsheet, the backsheet film, the backsheet nonwoven web, the landing zone, the stretch ear film, the back ear nonwoven web, the tape tabs, the ear hooks, the front ear nonwoven web, the waist feature nonwoven web, the waist feature elastics, the barrier leg cuff nonwoven web, the outer leg elastics, the acquisition material, the core cover nonwoven web, the chassis adhesives, or the core adhesives that comprises the bio-based polyolefin comprises at least about 50% by weight of polyolefin.

7. The absorbent article of claim 1, wherein the superabsorbent polymers are made at least in part from bio-based acrylic acid having a purity of about 98 weight % acrylic acid.

8. An absorbent article comprising the following enumerated components: (1) a topsheet; (2) a backsheet film; (3) a backsheet nonwoven web; (4) a landing zone; (5) a stretch ear film; (6) a back ear nonwoven web; (7) tape tabs; (8) ear hooks; (9) a front ear nonwoven web; (10) a waist feature nonwoven web; (11) waist feature elastics; (12) a barrier leg cuff nonwoven web; (13) outer leg elastics; (14) an acquisition material; (15) a core cover nonwoven web; (16) chassis adhesives; and (17) core adhesives;
   wherein the topsheet is joined to a backsheet defined by the backsheet film and the backsheet nonwoven web;
   wherein the core cover nonwoven web and a core absorbent material are positioned intermediate the topsheet and the backsheet; and
   wherein at least 13 of the 17 enumerated components of the absorbent article comprise one or more polyolefins;
   wherein at least 3 of the 13 components comprising one or more polyolefins comprise a bio-based polyolefin with:
      a bio-based content from 5% to 100% using ASTM D6866-10, method B; and
      a purity of about 98 weight % polyolefin and less than 2 weight % impurities; and
   wherein the core absorbent material comprises superabsorbent polymers with a bio-based content from about 5% to about 100% using ASTM D6866-10, method B; and
   wherein recycled polyolefin recovered from an entirety of the absorbent article via a recycling operation comprises a polyolefin content of at least about 90% by weight, based on a total weight of the absorbent article excluding the core absorbent material.

9. The absorbent article of claim 8, wherein at least 14 of the 17 enumerated components of the absorbent article comprise one or more polyolefins, and wherein at least 4 of the 14 components comprising one or more polyolefins comprise the bio-based polyolefin.

10. The absorbent article of claim 8, wherein at least 16 of the 17 enumerated components of the absorbent article comprise one or more polyolefins, and wherein at least 5 of the 16 components comprising one or more polyolefins comprise the bio-based polyolefin.

11. The absorbent article of claim 8, wherein at least one of the enumerated components that comprises one or more polyolefins comprises a bio-based polyolefin with a bio-based content from about 5% to about 100% using ASTM D6866-10, method B.

12. The absorbent article of claim 8, wherein at least five of the enumerated components that comprise one or more polyolefins comprise a bio-based polyolefin with a bio-based content from about 5% to about 100% using ASTM D6866-10, method B.

13. The absorbent article of claim 8, wherein the superabsorbent polymers are made at least in part from bio-based acrylic acid having a purity of about 98 weight % acrylic acid and wherein the absorbent article comprises a polyolefin content of at least about 95% by weight, based on the total weight of the absorbent article excluding the core absorbent material.

14. An absorbent article comprising the following enumerated components: (1) a topsheet; (2) a backsheet film; (3) a backsheet nonwoven web; (4) belt elastics; (5) a belt nonwoven web; (6) chassis adhesives; (7) a barrier leg cuff nonwoven web; (8) outer leg elastics; (9) an acquisition material; (10) a core cover nonwoven web; and (11) core adhesives;
    wherein the topsheet is joined to a backsheet defined by the backsheet film and the backsheet nonwoven web;
    wherein the core cover nonwoven web and a core absorbent material are positioned intermediate the topsheet and the backsheet;
    wherein at least 7 of the 11 enumerated components of the absorbent article comprise one or more polyolefins;
    wherein at least 3 of the 7 components comprising one or more polyolefins comprise a bio-based polyolefin with:
        a bio-based content from 5% to 100% using ASTM D6866-10, method B; and
        a purity of about 98 weight % polyolefin and less than 2 weight % impurities;
    wherein the core absorbent material comprises superabsorbent polymers with a bio-based content from about 5% to about 100% using ASTM D6866-10, method B; and
    wherein recycled polyolefin recovered from an entirety of the absorbent article via a recycling operation comprises a polyolefin content of at least about 90% by weight, based on a total weight of the absorbent article excluding the core absorbent material.

15. The absorbent article of claim 14, wherein at least 8 of the enumerated components of the absorbent article comprise one or more polyolefins, and wherein at least 4 of the 8 components comprising one or more polyolefins comprise the bio-based polyolefin.

16. The absorbent article of claim 14, wherein at least 10 of the enumerated components of the absorbent article comprise one or more polyolefins, and wherein at least 5 of the 10 components comprising one or more polyolefins comprise the bio-based polyolefin.

17. The absorbent article of claim 14, wherein at least one of the enumerated components that comprises one or more polyolefins comprises a bio-based polyolefin with a bio-based content from about 5% to about 100% using ASTM D6866-10, method B.

18. The absorbent article of claim 14, wherein at least five of the enumerated components that comprise one or more polyolefins comprise a bio-based polyolefin with a bio-based content from about 5% to about 100% using ASTM D6866-10, method B.

19. The absorbent article of claim 14, wherein the superabsorbent polymers are made at least in part from bio-based acrylic acid having a purity of about 98 weight % acrylic acid and wherein the absorbent article comprises a polyolefin content of at least about 95% by weight, based on the total weight of the absorbent article excluding the core absorbent material.

\* \* \* \* \*